United States Patent [19]

Scartazzini et al.

[11] 4,248,868
[45] Feb. 3, 1981

[54] CEPHEM CARBONYLMETHYL DERIVATIVES

[75] Inventors: Riccardo Scartazzini, Allschwil; Hans Bickel, Binningen, both of Switzerland

[73] Assignee: Ciba-Geigy Corporation, Ardsley, N.Y.

[21] Appl. No.: 14,454

[22] Filed: Feb. 23, 1979

Related U.S. Application Data

[63] Continuation of Ser. No. 715,084, Aug. 17, 1976, abandoned.

[30] Foreign Application Priority Data

Aug. 22, 1975 [CH] Switzerland ............... 10904/75

[51] Int. Cl.³ .............................. C07D 501/20
[52] U.S. Cl. ................................ 424/246; 544/16; 544/22; 544/23
[58] Field of Search ............... 544/22, 16, 27, 23

[56] References Cited

U.S. PATENT DOCUMENTS

| | | | |
|---|---|---|---|
| 3,823,139 | 7/1974 | Underwood | 544/16 |
| 3,823,140 | 7/1974 | Clark et al. | 544/16 |

*Primary Examiner*—Nicholas S. Rizzo
*Attorney, Agent, or Firm*—Prabodh I. Almaula

[57] ABSTRACT

The invention comprises carbonylmethyl derivatives of the formula IA and corresponding carbonylmethylene derivatives of the formula IB

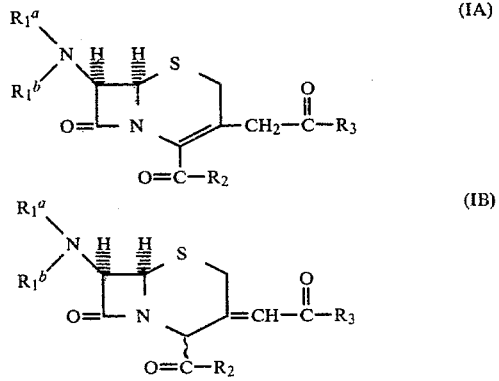

in which $R_1{}^a$ represents a member of the group comrising hydrogen and an acyl radical of the formula A $$R_a-C(R_b)(R_c)-C(=O)-\quad\quad (A)$$

in which $R_a$ represents a member of the group comprising optionally substituted phenyl, thienyl, furyl, cyclohexadienyl and cyclohexenyl, $R_b$ represents hydrogen and $R_c$ represents a member of the group comprising hydrogen, optionally protected hydroxyl, optionally protected amino and phenyl-lower protected sulpho, or in which $R_a$ represents a member of the group comprising cyano, optionally substituted phenoxy, pyridylthio, and tetrazolyl, and $R_b$ and $R_c$ each represent hydrogen, or in which $R_a$ represents a member of the group comprising phenyl, thienyl, furyl, and $R_b$ and $R_c$ together denote a member of the group comprising lower alkoxyimino, cycloalkoxyimino and phenyl-lower alkoxyimino in the syn-configuration, and such a group of the formula (A) contains at most one free amino group, $R_1{}^b$ represents hydrogen, $R_2$ represents a member of the group comprising hydroxyl, α-polybranched lower alkoxy and 2-halogeno-lower alkoxy, which can easily be converted into the latter, and also phenacyloxy, 1-phenyl-lower alkoxy which has 1–3 phenyl radicals which are optionally substituted by lower alkoxy or nitro, lower alkanoyloxymethoxy, α-amino-lower alkanoyloxymethoxy, or 2-phthalidyloxy, and also tris-lower alkylsilyloxy, and $R_3$ represents a member of the group comprising hydrogen, lower alkyl, cycloalkyl, phenyl which is optionally substituted by lower alkyl, lower alkoxy or halogen, phenyllower alkyl which is optionally substituted by nitro, lower alkyl, lower alkoxy or halogen, hydroxyl, etherified hydroxyl, especially lower alkoxy, above all methoxy, amino, lower alkylamino, di-lower alkylamino, lower alkyleneamino, oxa-lower alkylenamino, phenylamino, hydroxylamino, lower alkoxyamino, hydrazino, 2-lower alkylhydrazino, 2-phenylhydrazino, 4-lower alkylpiperazin-1-ylamino, lower alkylamino which is substituted by amino and/or carboxyl, and heterocyclylamino which is optionally substituted by lower alkyl, and wherein the heterocyclyl radical preferably contains 5–6 rings members and contains, as heteroatoms, nitrogen, which is optionally also in the N-oxidized form, oxygen or sulphur and 1-oxides and salts of such compounds, which compounds are active against microorganisms, such as Gram-positive and Gram-negative bacteria, and pharmaceutical preparations containing these compounds.

23 Claims, No Drawings

CEPHEM CARBONYLMETHYL DERIVATIVES

This is a continuation of application Ser. No. 715,084 filed on Aug. 17, 1976, now abandoned.

The present invention relates to carbonylmethyl derivatives, especially 7β-amino-3-cephem-3-carbonylmethyl-4-carboxylic acid compounds of the formula

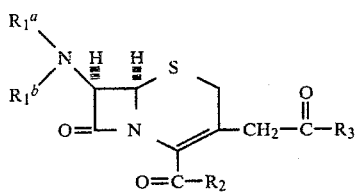
(IA)

wherein $R_1{}^a$ represents hydrogen or an amino protective group $R_1{}^A$ and $R_1{}^b$ represents hydrogen or an acyl group Ac, or $R_1{}^a$ and $R_1{}^b$ together represent a divalent amino protective group, $R_2$ represents hydroxyl or a radical $R_2{}^A$ which together with the carbonyl grouping —C(=O)— forms a protected carboxyl group and $R_3$ represents hydrogen, an optionally substituted hydrocarbon radical, an optionally substituted heterocyclic radical, optionally substituted hydroxyl or optionally substituted amino, corresponding 7β-amino-3-carbonylmethylene-cepham-4-carboxylic acid compounds of the formula

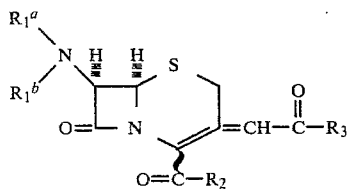
(IB)

wherein $R_1{}^a$, $R_1{}^b$, $R_2$ and $R_3$ have the abovementioned meanings, and 1-oxides and salts of such compounds and also processes for their manufacture.

An amino protective group $R_1{}^A$ is a group which can be replaced by hydrogen, above all an acyl group Ac, also a triarylmethyl group, especially the trityl group, as well as an organic silyl group or an organic stannyl group. An acyl group Ac, which can also represent a radical $R_1{}^b$, is, above all, the acyl radical of an organic carboxylic acid, preferably with up to 18 carbon atoms, especially the acyl radical of an optionally substituted aliphatic, cycloaliphatic, cycloaliphatic-aliphatic, aromatic, araliphatic, heterocyclic or heterocyclic-aliphatic carboxylic acid (including formic acid), as well as the acyl radical of a carbonic acid half-derivative.

An acyl radical Ac which can be split off easily and can be used as an amino protective group is, above all, an acyl radical of a half-ester of carbonic acid which can be split off by reduction, for example on treatment with a chemical reducing agent, or by treatment with acid, for example with trifluoroacetic acid, such as a lower alkoxycarbonyl radical which preferably has multiple branching and/or an aromatic substituent on the carbon atom in the α-position to the oxy group, or a methoxycarbonyl radical which is substituted by arylcarbonyl, especially benzoyl, for example tert.-butoxycarbonyl, tert.-pentoxycarbonyl or phenacyloxycarbonyl, or a lower alkoxycarbonyl radical which is substituted in the β-position by halogen atoms, for example 2,2,2-trichloroethoxycarbonyl or 2-iodoethoxycarbonyl, or a radical which can be converted into the latter, such as 2-chloro- or 2-bromo-ethoxycarbonyl, and also preferably polycyclic cycloalkoxycarbonyl, for example adamantyloxycarbonyl, optionally substituted phenyl-lower alkoxycarbonyl, above all α-phenyl-lower alkoxycarbonyl, wherein the α-position is preferably polysubstituted, for example diphenylmethoxy-carbonyl or α-4-biphenylyl-α-methyl-ethoxycarbonyl, or furyl-lower alkoxycarbonyl, above all α-furyl-lower alkoxycarbonyl, for example furfuryloxycarbonyl.

A divalent amino protective group formed by the radicals $R_1{}^a$ and $R_1{}^b$ together is, in particular, the divalent acyl radical of an organic dicarboxylic acid, preferably with up to 18 carbon atoms, above all the diacyl radical of an aliphatic or aromatic dicarboxylic acid, for example the acyl radical of a lower alkane- or lower alkene-dicarboxylic acid, such as succinyl, or of a o-arylenedicarboxylic acid, such as phthaloyl, or is also the acyl radical of an α-aminoacetic acid which is preferably substituted in the α-position and contains, for example, an aromatic or heterocyclic radical, and wherein the amino group is bonded to the nitrogen atom via a methylene radical which is preferably substituted and contains, for example, two lower alkyl groups, such as methyl groups, for example a 1-oxo-3-aza-1,4-butylene radical which is substituted, especially in the 2-position, and contains, for example, optionally substituted phenyl or thienyl, and is optionally monosubstituted or disubstituted, in the 4-position, by lower alkyl, such as methyl, for example 4,4-dimethyl-2-phenyl-1-oxo-3-aza-1,4-butylene.

The radicals $R_1{}^a$ and $R_1{}^b$ can also together represent an organic ylidene radical, such as an aliphatic, cycloaliphatic, cycloaliphatic-aliphatic or araliphatic ylidene radical, preferably with up to 18 carbon atoms.

An acyl group Ac in particular represents an acyl radical of an organic carboxylic acid, preferably with up to 18 carbon atoms, contained in a N-acyl derivative, which is naturally occurring or can be prepared biosynthetically, semi-synthetically or fully synthetically and is preferably pharmacologically active, of a 6-aminopenam-3-carboxylic acid compound or 7-amino-3-cephem-4-carboxylic acid compound.

An acyl radical Ac is, above all, a group of the formula $R_a$—C($R_b$)($R_c$)—C(=O)— (A), wherein $R_a$ represents optionally substituted phenyl, thienyl, such as 2- or 3-thienyl, furyl, such as 2-furyl, cyclohexadienyl, such as 1,4-cyclohexadienyl, or cyclohexenyl, such as 1-cyclohexenyl, $R_b$ represents hydrogen and $R_c$ represents hydrogen, optionally protected hydroxyl, optionally protected amino or optionally protected sulpho, or wherein $R_a$ represents cyano, optionally substituted phenoxy, pyridylthio, such as 4-pyridylthio, or tetrazolyl, such as 1-tetrazolyl, and $R_b$ and $R_c$ each represent hydrogen, or wherein $R_a$ represents phenyl, thienyl, such as 2-thienyl, or furyl, such as 2-furyl, and $R_b$ and $R_c$ together denote lower alkoxyimino, cycloalkoxyimino or phenyl-lower alkoxyimino in the syn-configuration, and such a group of the formula (A) contains at most one free amino group.

Substituents of the phenyl group and of the phenoxy group $R_a$ can be in the 2-, 3- or 4-position and comprise, for example, optionally substituted, such as protected or otherwise etherified or esterified, hydroxyl groups, such as free hydroxyl, for example 4-hydroxyl, lower alkoxy, for example 4-methoxy, lower alkanoyloxy, for example 4-acetoxy, aroyloxy, for example 4-benzoyloxy or 4-carbamoyloxy, halogen, such as 2-, or 3- or 4-chloro, optionally substituted, such as protected, lower alkylated or sulphonylated amino groups, such as free amino, methylamino or dimethylamino, or lower alkylsulphonylamino, such as 3-methylsulphonylamino, and optionally protected aminomethyl, such as 3-aminomethyl or 3-tert.-butoxycarbonylaminomethyl.

Substituents of the thienyl, furyl, cyclohexadienyl and cyclohexenyl groups $R_a$ are, for example, optionally protected aminomethyl groups, which in a 2-thienyl and 2-furyl group are, in particular, in the 5-position and in a 1,4-cyclohexadienyl and 1-cyclohexyl group are, in particular, in the 2- or 3-position.

Protected hydroxyl groups, protected amino groups and protected sulpho groups in acyl groups of the formula (A) are those which are customary in cephalosporin chemistry and which can be converted into free hydroxyl groups and free amino groups respectively without the cephem skeleton being destroyed or other undesired side reactions taking place.

A radical which can be split off easily and can be used as a hydroxyl protective group is, above all, an acyl radical of a half-ester of carbonic acid which can be split off by reduction, for example on treatment with a chemical reducing agent, or by treatment with acid, for example with trifluoroacetic acid, such as a lower alkoxycarbonyl radical which preferably has multiple branching and/or an aromatic substituent on the carbon atom in the α-position to the oxy group, or a methoxycarbonyl radical which is substituted by arylcarbonyl, especially benzoyl, or a lower alkoxycarbonyl radical which is substituted in the β-position by halogen atoms, for example tert.-butoxycarbonyl, tert.-pentoxycarbonyl, phenacyloxycarbonyl, 2,2,2-trichloroethoxycarbonyl or 2-iodoethoxycarbonyl or a radical which can be converted into the latter, such as 2-chloro- or 2-bromoethoxycarbonyl, and also preferably polycyclic cycloalkoxycarbonyl, for example adamantyloxycarbonyl, optionally substituted phenyl-lower alkoxycarbonyl, such as p-nitrobenzyloxycarbonyl, or, above all, α-phenyl-lower alkoxycarbonyl, wherein the α-position is preferably polysubstituted, for example diphenylmethoxycarbonyl or α-4-biphenylyl-α-methyl-ethoxycarbonyl, or furyl-lower alkoxycarbonyl, above all α-furyl-lower alkoxycarbonyl, for example furfuryloxycarbonyl.

Another hydroxyl protective group is, for example, a 2-oxa- or 2-thia-aliphatic or -cycloaliphatic hydrocarbon radical which can be split off easily, above all a 1-lower alkoxy-1-lower alkyl or 1-lower alkylthio-1-lower alkyl radical, such as 1-methoxy-1-ethyl, 1-ethoxy-1-ethyl, 1-methylthio-1-ethyl or 1-ethylthio-1-ethyl, or a 2-oxa- or 2-thia-cyclo-lower alkyl or -cyclo-lower alkenyl radical with 5–7 ring atoms, such as 2-tetrahydrofuryl, 2-tetrahydropyranyl or 2,3-dihydro-2-pyranyl, or a corresponding thia analogue.

A further hydroxyl protective group is a substituted silyl or stannyl group which can be split off easily and which is preferably substituted by optionally substituted aliphatic, cycloaliphatic, aromatic or aralphatic hydrocarbon radicals, such as lower alkyl, halogeno-lower alkyl, cycloalkyl, phenyl or phenyl-lower alkyl groups, or optionally modified functional groups, such as etherified hydroxyl groups, for example lower alkoxy groups, or halogen atoms, for example chlorine atoms, such as, above all, tri-lower alkylsilyl, for example trimethylsilyl, halogeno-lower alkoxy-lower alkylsilyl, for example chloromethoxymethylsilyl, or tri-lower alkylstannyl, such as tri-n-butylstannyl.

A further hydroxyl protective group is also an optionally substituted α-phenyl-lower alkyl group which can also be split off easily, such as an optionally substituted benzyl or diphenylmethyl group, possible substituents of the phenyl nuclei being, for example, esterified or etherified hydroxyl, such as halogen, for example fluorine, chlorine or bromine, or lower alkoxy, such as methoxy, or nitro.

An amino protective group in an acyl group of the formula (A) is, for example, any of the groups listed under $R_1^4$ which can be replaced by hydrogen, and especially groups which can be split off easily, and is, in particular, tert.-butoxycarbonyl or 2,2,2-trichloroethoxycarbonyl.

A protected sulpho group is, above all, a sulpho group esterified with an aliphatic, cycloaliphatic, cycloaliphatic-aliphatic, aromatic or aralphatic alcohol or with a silyl or stannyl alcohol. In a sulpho group, the hydroxyl group can be etherified, for example like the hydroxyl group in the carboxyl group —C(=O)—$R_2^A$.

Acyl radicals of the formula (A) which are to be singled out are, for example, cyanoacetyl, tetrazol-1-ylacetyl, 4-pyridylthioacetyl, phenoxyacetyl, phenylacetyl, 4-methoxyphenylacetyl, 3- or 4-chlorophenylacetyl, 3-methylsulphonylaminophenylacetyl, 2- or 3-thienylacetyl, 2-(5-aminomethyl-2-thienyl)-acetyl, 2-furylacetyl, 2-(5-aminomethyl-2-furyl)-acetyl, 1,4-cyclohexadienylacetyl, 2-(2-aminomethyl-1,4-cyclohexadienyl)-acetyl, 1-cyclohexenylacetyl, 2-(2-aminomethyl-1-cyclohexenyl)-acetyl, D-mandeloyl, α-hydroxy-2-thienylacetyl, α-hydroxy-1,4-cyclohexadienylacetyl and, in particular, D(−)-phenylglycyl, 4-hydroxy-D(−)-phenylglycyl, 4-methoxy-D(−)-phenylglycyl, 3-methylsulphonylamino-D(−)-phenylglycyl, D(−)-2- or D(−)-3-thienylglycyl, D(−)-2-furylglycyl, D(−)-1,4-cyclohexadienylglycyl or D(−)-1-cyclohexenylglycyl, and also α-sulpho-phenylacetyl as well as α-phenyl-α-syn-methoxyimino-acetyl, α-(2-thienyl)-α-syn-methoxyimino-acetyl or α-(2-furyl)-α-syn-methoxyimino-acetyl.

A protected carboxyl group of the formula —C(=O)—$R_2^A$ is, above all, an esterified carboxyl group wherein $R_2^A$ is a hydroxyl group etherified by an organic radical or by an organic silyl or stannyl group, or is also an optionally substituted hydrazinocarbonyl group. Organic radicals of this type are, for example, aliphatic, cycloaliphatic, cycloaliphatic-aliphatic, aromatic or aralphatic radicals, especially optionally substituted hydrocarbon radicals of this type as well as heterocyclic or heterocyclic-aliphatic radicals, preferably with up to 18 carbon atoms.

An etherified hydroxyl group $R_2^A$ forms, together with the carbonyl grouping, an esterified carboxyl group which can preferably be split easily, for example by reduction, such as by hydrogenolysis, or solvolytically, such as by acidolysis or hydrolysis, or can be converted easily into another functionally modified carboxyl group, such as into a hydrazinocarbonyl group. Such a group $R_2^A$ is, for example, 2-halogeno-lower alkoxy, wherein halogen preferably has an atomic weight of more than 19, for example 2,2,2-trichloroethoxy or 2-iodoethoxy, and also 2-chloroethoxy or 2-bromoethoxy which can easily be converted into 2-iodoethoxy, or $R_2^A$ is a methoxy group which is polysubstituted by optionally substituted hydrocarbon radicals, especially aliphatic or aromatic hydrocarbon radicals, such as lower alkyl, for example methyl, and/or phenyl, or is monosubstituted by a carbocyclic aryl group which contains electron-donating substituents or by a heterocyclic group of aromatic character which contains oxygen or sulphur as a ring member, such as tert.-lower alkoxy, for example tert.-butoxy or tert.-pentoxy, optionally substituted diphenylmethoxy, for example diphenylmethoxy or 4,4'-dimethoxydiphenylmethoxy, lower alkoxyphenyl-lower alkoxy, for example lower alkoxybenzyloxy, such as methoxybenzyloxy (in which methoxy is above all in the 3-, 4- and/or 5-position), above all 3- or 4-methoxybenzyloxy or 3,4-dimethoxybenzyloxy, or, above all, nitrobenzyloxy, for example 4-nitrobenzyloxy, 2-nitrobenzyloxy or 4,5-dimethoxy-2-nitrobenzyloxy, or furfuryloxy, such as 2-furfuryloxy, or $R_2^A$ is 2-oxa- or 2-thia-cycloalkoxy or -cycloalkenyloxy with 5–7 ring members, such as 2-tetrahydrofuryloxy, 2-tetrahydropyranyloxy or 2,3-dihydro-2-pyranyloxy, or a corresponding thia analogue, or $R_2^A$ is arylcarbonylmethoxy wherein aryl in particular represents an optionally substituted phenyl group, for example phenacyloxy, or $R_2^A$, together with the —C(=O)— grouping, forms an activated ester group and is, for example, nitrophenoxy, for example 4-nitrophenoxy or 2,4-dinitrophenoxy.

An organic silyloxy or organic stannyloxy group $R_2^A$ is, in particular, a silyloxy or stannyloxy group which is substituted by 1 to 3 optionally substituted hydrocarbon radicals, preferably with up to 18 carbon atoms. It preferably contains, as substituents, aliphatic, cycloaliphatic, aromatic or araliphatic hydrocarbon radicals which are optionally substituted, for example which are substituted by lower alkoxy, such as methoxy, or by halogen, such as chlorine, such as lower alkyl, halogeno-lower alkyl, cycloalkyl, phenyl or phenyl-lower alkyl, and is, above all, tri-lower alkylsilyloxy, for example trimethylsilyloxy, halogenolower alkoxy-lower alkylsilyloxy, for example chloromethoxy-methylsilyloxy, or tri-lower alkylstannyloxy, for example tri-n-butylstannyloxy.

The group $R_2^A$ can also be an etherified hydroxyl group which, together with the carbonyl grouping —C(=O)—, forms an esterified carboxyl group which can be split under physiological conditions, above all an acyloxymethoxy group, wherein acyl denotes, for example, the radical of an organic carboxylic acid, above all of an optionally substituted lower alkanecarboxylic acid, or wherein acyloxymethyl forms the residue of a lactone. Hydroxyl groups etherified in this way are lower alkanoyloxy-methoxy, for example acetyloxymethoxy or pivaloyloxymethoxy, amino-lower alkanoyloxymethoxy, especially α-amino-lower alkanoyloxymethoxy, for example glycyloxymethoxy, L-valyloxymethoxy, L-leucyloxymethoxy and also phthalidyloxy.

A radical $R_2^A$ which, together with a —C(=O)— grouping, forms an optionally substituted hydrazinocarbonyl group is, for example, hydrazino or 2-lower alkylhydrazino, for example 2-methylhydrazino.

A hydrocarbon radical $R_3$ is an optionally substituted aliphatic, cycloaliphatic, cycloaliphatic-aliphatic, aromatic, araliphatic or heterocyclic-aliphatic radical with, preferably, up to 18, and especially up to 7, carbon atoms.

An aliphatic radical $R_3$ is, for example, unbranched or branched lower alkyl with 1 to 7, and especially 1 to 4, carbon atoms, such as methyl, ethyl, propyl, butyl, pentyl, hexyl or isopropyl, isobutyl or tert.-butyl.

A cycloaliphatic radical $R_3$ is, for example, cycloalkyl with 3 to 7 carbon atoms, such as cyclopropyl, cyclobutyl, cyclopentyl or cyclohexyl.

A cycloaliphatic-aliphatic radical $R_3$ contains, for example, 4 to 7 carbon atoms and is, for example, cyclopropylmethyl, cyclobutylmethyl, cyclopentylmethyl or cyclohexylmethyl.

An aromatic radical $R_3$ is, for example, monocyclic or bicyclic aryl, such as phenyl or naphthyl.

An araliphatic radical $R_3$ is, for example, aryl-lower alkyl, such as phenyl-lower alkyl, for example phenylmethyl or phenylethyl.

A heterocyclic-aliphatic radical $R_3$ is, for example, heterocyclyl-lower alkyl, wherein heterocyclyl has one of the meanings indicated below for a heterocyclic radical $R_3$ and lower alkyl in particular denotes methyl.

A heterocyclic radical $R_3$ is preferably of aromatic character, contains 5 or 6 ring members and 1 to 4 nitrogen atoms and/or an oxygen atom or a sulphur atom and is, for example, pyrryl, such as 2- or 3-pyrryl, pyridyl, such as 2-, 3- or 4-pyridyl, thienyl, such as 2- or 3-thienyl, furyl, such as 2-furyl, imidazolyl, such as 2-imidazolyl, pyrimidinyl, such as 2- or 4-pyrimidinyl, triazolyl, such as 1,2,4-triazol-3-yl, tetrazolyl, such as 1- or 5-tetrazolyl, oxazolyl, such as 2-oxazolyl, isoxazolyl, such as 3- or 4-isoxazolyl, thiazolyl, such as 2-thiazolyl, isothiazolyl, such as 3- or 4-isothiazolyl, or thiadiazolyl, such as 1,2,4-thiadiazol-3-yl or 1,3,4-thiadiazol-2-yl.

Substituents of the hydrocarbon and hetrocyclic radicals $R_3$ are, in particular, lower alkyl, such as methyl, lower alkoxy, such as methoxy, or halogen, such as chlorine.

A substituted hydroxyl group $R_3$ is, in particular, a hydroxyl group etherified by an organic radical or by an organic silyl or stannyl group and in particular is lower alkoxy with 1–7, and preferably 1–4, carbon atoms, such as methoxy or isobutoxy, and can moreover have the same meaning as the etherified hydroxyl group $R_2^A$, for example diphenylmethoxy or nitrobenzyloxy.

A substituted amino group $R_3$ carries as substituents one or two monovalent or divalent hydrocarbon radicals, preferably with up to 18 carbon atoms, which are optionally substituted, such as substituted by lower alkyl, optionally etherified or esterified hydroxyl, amino and/or carboxyl, such as corresponding aliphatic, cycloaliphatic, cycloaliphatic-aliphatic, aromatic, hetero-aromatic or araliphatic hydrocarbon radicals, or a hydroxyl or amino group which is optionally substituted, such as lower alkylated. A substituted amino group $R_3$ of this type is, for example, lower alkylamino, such as methylamino or ethylamino, di-lower alkylamino, such as dimethylamino or diethylamino, lower alkyleneamino, such as pyrrolidino or piperidino, oxa-lower alkyleneamino, such as morpholino, phenylamino, hydroxylamino, lower alkoxyamino, such as methoxyamino, hydrazino, 2-lower alkylhydrazino, such as 2-methylhydrazino, 2,2-di-lower alkylhydrazino, such as 2,2-dimethylhydrazino, 2-phenylhydrazino, 4-lower alkyl-piperazin-1-ylamino, such as 4-methylpiperazin-1-ylamino, lower alkylamino which is substituted by amino and/or carboxyl, such as 5-amino-5-carboxy-pentylamino, or heterocyclylamino which is optionally substituted, especially by lower alkyl, and wherein the heterocyclyl radical preferably contains 5–6 ring members and contains, as heteroatoms, nitrogen, which is optionally also in the N-oxidised form, oxygen or sulphur, such as, for example, optionally 1-oxidised pyridyl, pyrazinyl, pyrimidyl, pyridazinyl, thiadiazolyl, 2-methylthiadiazolyl, oxadiazolyl, tetrazolyl or N-methyltetrazolyl.

Salts are, in particular, those of compounds of the formulae IA and IB having an acid grouping, such as a carboxyl group, above all metal salts or ammonium salts, such as alkali metal salts and alkaline earth metal salts, for example sodium, potassium, magnesium or calcium salts, as well as ammonium salts with ammonia or suitable organic amines, compounds which can be used for forming the salts being, above all, aliphatic, cycloaliphatic, cycloaliphaticaliphatic and araliphatic primary, secondary or tertiary monoamines, diamines or polyamines, as well as heterocyclic bases, such as lower alkylamines, for example triethylamine, hydroxy-lower alkylamines, for example 2-hydroxyethylamine, bis-(2-hydroxyethyl)-amine or tris-(2-hydroxyethyl)-amine, basic aliphatic esters of carboxylic acids, for example 2-diethylaminoethyl 4-aminobenzoate, lower alkyleneamines, for example 1-ethyl-piperidine, cycloalkylamines, for example bicyclohexylamine, or benzylamines, for example N,N'-dibenzylethylenediamine, and also bases of the pyridine type, for example pyridine, collidine or quinoline. Compounds of the formulae IA and IB which contain a basic group can also form acid addition salts, for example with inorganic acids, such as hydrochloric acid, sulphuric acid or phosphoric acid, or with suitable organic carboxylic or sulphonic acids, for example trifluoroacetic acid or p-toluenesulphonic acid. Compounds of the formulae IA and IB which have an acid group and a basic group can also be in the form of inner salts, that is to say in the form of a zwitter-ion. 1-Oxides of compounds of the formula IA which have salt-forming groups can also form salts, as described above. Pharmaceutically acceptable salts are preferred.

The compounds of the present invention possess valuable pharmacological properties or can be used as intermediate products for the manufacture of such compounds. Compounds of the formula IA, wherein, for example, $R_1^a$ represents an acyl radical Ac occurring in pharmacologically active N-acyl derivatives of 6β-amino-penam-3-carboxylic acid compounds or 7β-amino-3-cephem-4-carboxylic acid compounds and $R_1^b$ represents hydrogen, or wherein $R_1^a$ and $R_1^b$ together represent a 1-oxo-3-aza-1,4-butylene radical which is preferably substituted in the 2-position, for example by an aromatic or heterocyclic radical, and preferably substituted in the 4-position, for example by 2 lower alkyls, such as methyl, $R_2$ denotes hydroxyl or an etherified hydroxyl group $R_2^A$ which, together with the carbonyl group, forms an esterified carboxyl group which can be split easily under physiological conditions, and $R_3$ has the meaning indicated under formula IA, and functional groups which may be present in an acyl radical $R_1^a$ and in a radical $R_3$, such as amino, carboxyl, hydroxyl an/or sulpho, are usually in the free form, or pharmacologically acceptable salts of such compounds having salt-forming groups, inhibit, for example, the growth of Gram-positive germs, such as *Staphylococcus aureus*, and enterobacteriaceae, such as *Escherichia coli*, *Klebsiella pneumonia* or *Salmonella typhimurium*, in vitro in concentrations of about 0.1 mcg/ml to about 50 mcg/ml. In vivo, they are effective, on oral administration, against microorganisms, such as Gram-positive bacteria, for example *Staphylococcus aureus* (for example in mice at doses of 0.003 g/kg to 0.045 g/kg given perorally) and Gram-negative bacteria, for example *Escherichia coli* (for example in mice at doses of 0.065 g/kg to 0.300 g/kg given perorally), and especially also against penicillin-resistant bacteria, and are of low toxicity. These new compounds, and especially those which are preferred, for example 3-carbomethoxymethyl-7β-[D(−)-α-phenylglycylamino]-3-cephem-4-carboxylic acid, or their pharmacologically acceptable salts, can therefore be used, for example in the form of formulations which have an antibiotic action, for the treatment of corresponding systemic infections and also as feedstuff additives, for preserving foodstuffs and as disinfectants.

Compounds of the formula IB or 1-oxides of compounds of the formula IA or IB, wherein $R_1^a$, $R_1^b$, $R_2$ and $R_3$ have the meanings indicated in the context of formula IA, or compounds of the formula IA wherein $R_3$ has the abovementioned meaning, the radicals $R_1^a$ and $R_1^b$ represent hydrogen, or $R_1^a$ denotes an amino protective group which differs from an acyl radical occurring in pharmacologically active N-acyl derivatives of 6β-amino-penam-3-carboxylic acid compounds or 7β-amino-3-cephem-4-carboxylic acid compounds and $R_1^b$ denotes hydrogen, or $R_1^a$ and $R_1^b$ together represent a divalent amino protective group which differs from a 1-oxo-3aza-1,4-butylene radical which is preferably substituted in the 2-position, for example by an aromatic or heterocyclic radical, and preferably substituted in the 4-position, for example by 2 lower alkyls, such as methyl, and $R_2$ represents hydroxyl, or $R_1^a$ and $R_1^b$ have the abovementioned meanings, $R_2$ represents a radical $R_2^A$ which, together with the —C(=O)— grouping forms a protected carboxyl group, which preferably can be split easily, a carboxyl group protected in this way differing from a physiologically splittable carboxyl group, and $R_3$ has the abovementioned meanings, are valuable intermediate products which can be converted in a simple manner, for example as will be described below, into the abovementioned pharmacologically active compounds.

The main significance of 1-oxides of compounds of the formula IA and IB lies in the isomerization of 3-carbonylmethylene-cepham compounds of the formula IB to the 3—carbonylmethyl-3-cephem compounds of the formula IA, because 1-oxides of 3-carbonylmethylene-cepham compounds can easily be rearranged, in polar solvents, to the 1-oxides of the corresponding 3-carbonylmethyl-3-cepham compounds, which can be reduced in a simple manner, as described below.

The invention relates in particular to the 3-cephem compounds of the formula IA wherein $R_1^a$ denotes hydrogen or, preferably, an acyl radical contained in a fermentatively obtainable (that is to say naturally occurring) or biosynthetically, semi-synthetically or fully synthetically obtainable, in particular pharmacologically active, such as highly active, N-acyl derivative of a 6β-amino-penam-3-carboxylic acid compound or 7β-amino-3-cephem-4-carboxylic acid compound, such as one of the abovementioned acyl radicals of the formula (A), in which formula $R_a$, $R_b$ and $R_c$ above all have the meanings which have been singled out and $R_1^b$ represents hydrogen, or wherein $R_1^a$ and $R_1^b$ together represent a 1-oxo-3-aza-1,4-butylene radical which is preferably substituted in the 2-position, for example by an aromatic or heterocyclic radical, such as phenyl, and preferably substituted in the 4-position, for example by two lower alkyls, such as methyl, $R_2$ represents hydroxyl, a hydroxyl group etherified by an organic radical or by an organic silyl or stannyl group or represents an optionally substituted hydrazino group $R_2^A$ and $R_3$ represents hydrogen, lower alkyl, a hydroxyl group, which is optionally etherified by an organic radical, or an optionally substituted amino group, and also the corresponding 3-carbonylmethylene-cepham compounds of the formula IB, as well as 1-oxides and salts of such compounds having salt-forming groups.

Above all, in a 3-cephem compound of the formula IA, and in a corresponding 3-carbonylmethylene-cepham compound of the formula IB, and also in a 1-oxide or in a salt of such a compound having salt-forming groups, $R_1{}^a$ represents hydrogen or an acyl radical of the formula (A), wherein $R_a$ above all has the meanings which have been singled out and, for example, represents phenyl which is optionally substituted by hydroxyl, protected hydroxyl, lower alkoxy, lower alkanoyloxy, carbamoyloxy, halogen, lower alkylsulphonylamino or aminomethyl, or thienyl, furyl, cyclohexadienyl or cyclohexenyl, which are optionally substituted by aminomethyl, $R_b$ represents hydrogen, and $R_c$ represents hydrogen, optionally protected hydroxyl, optionally protected amino or optionally protected sulpho, or wherein $R_a$ represents cyano, 1-tetrazolyl, phenoxy optionally substituted by the same substituents as the above mentioned phenyl residue $R_a$, or 4-pyridylthio and $R_b$ and $R_c$ each represent hydrogen, or wherein $R_a$ represents phenyl, 2-thienyl or 2-furyl, and $R_b$ and $R_c$ together denote syn-lower alkoxyimino, and such a group of the formula (A) contains at most one free amino group, $R_1{}^b$ represents hydrogen, $R_2$ represents hydroxyl, α-poly-branched lower alkoxy, for example tert.-butoxy, or 2-halogeno-lower alkoxy, for example 2,2,2-trichloroethoxy, 2-iodoethoxy, or 2-chloroethoxy or 2-bromoethoxy which can easily be converted into the latter, and also phenacyloxy, 1-phenyl-lower alkoxy which has 1–3 phenyl radicals which are optionally substituted by lower alkoxy or nitro, for example 4-methoxybenzyloxy, 4-nitrobenzyloxy, diphenylmethoxy, 4,4'-dimethoxydiphenylmethoxy or trityloxy, lower alkanoyloxymethoxy, for example acetoxymethoxy or pivaloyloxymethoxy, α-amino-lower alkanoyloxymethoxy, for example glycyloxymethoxy, or 2-phthalidyloxy, and also tri-lower alkylsilyloxy, for example trimethylsilyloxy, and $R_3$ represents hydrogen, lower alkyl, cycloalkyl, phenyl which is optionally substituted by lower alkyl, lower alkoxy or halogen, phenyl-lower alkyl which is optionally substituted by lower alkyl, lower alkoxy or halogen, hydroxyl, etherified hydroxyl, especially lower alkoxy, such as methoxy or isobutoxy, or such as has been defined under the etherified hydroxyl group $R_2{}^A$, amino, lower alkylamino, di-lower alkylamino, lowr alkyleneamino, oxa-lower alkyleneamino, phenylamino, hydroxylamino, lower alkoxyamino, hydrazino, 2-lower alkylhydrazino, 2-phenylhydrazino, 4-lower alkylpiperazin-1-ylamino, lower alkylamino which is substituted by amino and/or carboxyl, such as 5-amino-5-carboxypentylamino, or heterocyclylamino which is optionally substituted, especially by lower alkyl, and wherein the heterocyclyl radical preferably contains 5–6 ring members and contains, as hetero-atoms, nitrogen, which is optionally also in the N-oxidised form, oxygen or sulphur, such as, for example, optionally 1-oxidised pyridyl, pyrazinyl, pyrimidyl, pyridazinyl, thiadiazolyl, 2-methylthiadiazolyl, oxadiazolyl, tetrazolyl or N-methyltetrazolyl.

The invention relates above all to 3-cephem compounds of the formula IA, wherein $R_1{}^a$ represents hydrogen or, in particular, an acyl group of the formula (A), wherein $R_a$ denotes phenyl, hydroxyphenyl, for example 3- or 4-hydroxyphenyl, 3-lower alkylsulphonylaminophenyl, for example 3-methylsulphonylaminophenyl, or aminomethylphenyl, it being possible, in such radicals, for hydroxyl and/or amino to be protected by acyl radicals, such as optionally halogenated lower alkoxycarbonyl radicals, for example tert.-butoxycarbonyl or 2,2,2-trichloroethoxycarbonyl, and also denotes thienyl, for example 2- or 3-thienyl, aminomethylthienyl, for example 5-aminomethyl-2-thienyl, furyl, for example 2-furyl, amino-methylfuryl, for example 5-aminomethyl-2-furyl, 1,4-cyclohexadienyl, aminomethyl-1,4-cyclohexadienyl, for example 2-aminomethyl-1,4-cyclohexadienyl, 1-cyclohexenyl or aminomethyl-1-cyclohexenyl, for example 2-aminomethyl-1-cyclohexenyl, $R_b$ represents hydrogen and $R_c$ represents hydrogen, amino, as well as protected amino, such as acylamino, for example α-poly-branched lower alkoxycarbonylamino, such as tert.-butoxycarbonylamino or 2-halogeno-lower alkoxycarbonylamino, for example 2,2,2-trichloroethoxycarbonylamino, 2-iodoethoxycarbonylamino or 2-bromoethoxycarbonylamino, or phenyl-lower alkoxycarbonylamino which is optionally substituted by lower alkoxy or nitro, for example 4-methoxybenzyloxycarbonylamino or diphenylmethoxycarbonylamino, or represents hydroxyl, as well as protected hydroxyl, such as acyloxy, for example β-poly-branched lower alkoxycarbonyloxy, such as tert.-butoxycarbonyloxy, or 2-halogeno-lower alkoxycarbonyloxy, such as 2,2,2-trichloroethoxycarbonyloxy, 2-iodoethoxycarbonyloxy or 2-bromoethoxycarbonyloxy, and also formyloxy, or represents sulpho, or wherein $R_a$ represents cyano, 1-tetrazolyl, phenoxy or 4-pyridylthio and $R_b$ and $R_c$ each represent hydrogen, or wherein $R_a$ represents phenyl, 2-thienyl or 2-furyl and $R_b$ and $R_c$ together denote syn-lower alkoxyimino, such as syn-methoxyimino, and such a group of the formula (A) contains at most one free amino group, $R_1{}^b$ denotes hydrogen, $R_2$ above all represents hydroxyl and also represents α-poly-branched lower alkoxy, for example tert.-butoxy, 2-halogeno-lower alkoxy, for example 2,2,2-trichloroethoxy, 2-iodoethoxy or 2-bromoethoxy, or diphenylmethoxy which is optionally substituted, for example by lower alkoxy, such as methoxy, for example diphenylmethoxy or 4,4'-dimethoxydiphenylmethoxy, or p-nitrobenzyloxy, and also tri-lower alkylsilyloxy, for example trimethylsilyloxy, and $R_3$ denotes hydrogen, lower alkyl with 1 to 4 carbon atoms, such as methyl, or phenyl, hydroxyl, lower alkoxy, such as methoxy, ethoxy, isobutoxy or tert.-butoxy, or 2-halogeno-lower alkoxy, optionally substituted diphenylmethoxy, benzyloxy which is optionally substituted by methoxy and/or nitro, or amino, lower alkylamino, such as methylamino, di-lower alkylamino, such as dimethylamino or diethylamino, lower alkyleneamino, oxa-lower alkyleneamino, phenylamino, hydroxylamino, lower alkoxyamino, such as methoxyamino, hydrazino, 2-lower alkylhydrazino, 2-phenylhydrazino, 4-lower alkylpiperazin-1-ylamino, aminocarboxy-lower alkyl, such as 5-amino-5-carboxypentyl, pyridyl, pyrazinyl, pyrimidyl, pyridazinyl, thiadiazolyl, 2-methylthiadiazolyl, oxadiazolyl, tetrazolyl or N-methyltetrazolyl, and also to the corresponding 3-carbonylmethylene-cepham compounds of the formula IB, as well as the 1-oxides and salts, especially the non-toxic salts which can be used pharmacologically, such as the alkali metal salts, for example sodium salts, or alkaline earth metal salts, for example calcium salts, or ammonium salts, including those with amines, and the inner salts, of compounds wherein $R_2$ represents hydroxyl.

The invention relates above all to 7β-($R_a$-acetylamino)-, 7β-(D-α-hydroxy-α-$R_a$-acetylamino)- and, in particular, 7β-(D-α-amino-α-$R_a$-acetylamino)-3-$R_3$-carbonylmethyl-3-cephem-4-carboxylic acids, wherein $R_a$ represents phenyl, 4-hydroxyphenyl, 3-methylsulphonylaminophenyl, phenoxy, 2-thienyl, 5-aminomethyl-2-thienyl, 1,4-cyclohexadienyl or 1-cyclohexenyl, and $R_3$ represents methyl, methoxy, isobutoxy, phenyl, amino, dimethylamino, diethylamino, phenylamino, pyrrolidino, morpholino, hydrazino, 2-phenylhydrazino, 4-methylpiperazin-1-ylamino, 2-methylthiadiazolylamino or N-methyltetrazolylamino, and the pharmacologically acceptable salts thereof, and above all to 3-carbomethoxymethyl-7β-(D-α-amino-α-$R_a$-acetylamino)-3-cephem-4-carboxylic acids, wherein $R_a$ represents phenyl, 3-methylsulphonylaminophenyl or 1,4-cyclohexadienyl, and pharmacologically acceptable salts thereof; in the abovementioned concentrations, and especially on oral administration, these compounds display excellent antibiotic properties, both against Gram-positive bacteria and especially against Gram-negative bacteria, and are of low toxicity.

Compounds of the formula IA and IB, their 1-oxides and their salts are manufactured in a manner which is in itself known by reacting a compound of the formula

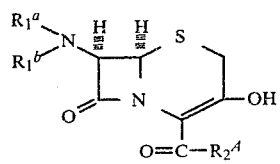

(II)

wherein $R_1{}^a$, $R_1{}^b$ and $R_2{}^A$ have the meanings indicated under formula I, or a 1-oxide thereof, with an ylide of the formula III

(III)

wherein $R_3$ has the meaning indicated under formula I and $X^\oplus$ denotes a trisubstituted phosphonium group or a diesterified phosphono group together with a cation, and, if desired or necessary, in a resulting compound of the formula IA or IB, converting the protected carboxyl group of the formula —C(=O)—$R_2{}^A$ into a free carboxyl group or into another protected carboxyl group, and/or, if desired, within the definition of the end products, converting a resulting compound into another compound, and/or, if desired, converting a resulting compound having a salt-forming group into a salt, or converting a resulting salt into the free compound or into another salt, and/or, if desired, separating a resulting mixture of isomeric compounds into the individual isomers.

The starting compound of the formula II is in equilibrium with the 3-oxo-cepham-4-carboxylic acid compound which is isomeric therewith and the latter is continuously removed from the equilibrium by reaction with the ylide. In a starting material of the formula II, the radical $R_1{}^a$ preferably denotes hydrogen or an amino protective group $R_1{}^A$, such as an acyl group Ac, wherein any free functional groups which may be present, for example amino, hydroxyl, carboxyl or sulpho groups, can be protected in a manner which is in itself known, amino groups, for example, by the abovementioned acyl, trityl, silyl or stannyl radicals and by substituted thio or sulphonyl radicals, and hydroxyl, carboxyl or sulpho groups, for example, by the abovementioned ether or ester groups, including silyl or stannyl groups, and $R_1{}^b$ preferably denotes hydrogen.

In a starting material of the formula II, $R_2{}^A$ preferably represents an etherified hydroxyl group which, together with the —C(=O)— grouping, forms an esterified carboxyl group which can be split, especially under mild conditions, and any functional groups which may be present in a carboxyl protective group $R_2{}^A$ can be protected in a manner which is in itself known, for example as indicated above. A group $R_2{}^A$ is, for example, in particular α-poly-branched lower alkoxy, for example tert.-butoxy, or 2-halogeno-lower alkoxy, wherein halogen represents, for example, chlorine, bromine or iodine, above all 2,2,2-trichloroethoxy, 2-bromoethoxy or 2-iodoethoxy, or an optionally substituted 1-phenyl-lower alkoxy group, such as a 1-phenyl-lower alkoxy group which contains lower alkoxy, for example methoxy, or nitro, such as benzyloxy or diphenylmethoxy which are optionally substituted, for example as indicated, for example benzyloxy, 4-methoxybenzyloxy, 4-nitrobenzyloxy, diphenylmethoxy or 4,4'-dimethoxydiphenylmethoxy, and also an organic silyloxy or stannyloxy group, such as tri-lower alkylsilyloxy, for example trimethylsilyloxy.

In an ylide of the formula III, $R_3$ is, in particular, one of the preferred hydrocarbon radicals, one of the preferred substituted hydroxyl groups or one of the preferred optionally substituted amino groups and the group $X^\oplus$ is one of the phosphonium or phosphono groups customary in condensation reactions analogous to the Wittig reaction, especially a triarylphosphonium group, such as a triphenylphosphonium group, or a tri-lower alkylphosphonium group, such as a tributylphosphonium group, or a phosphono group which is dietherified by lower alkyl, such as ethyl, and triphenylphosphonium and diethylphosphono are preferred and, in the case of the phosphono group, the symbol $X^\oplus$ also comprises the cation of a strong base.

In phosphonium compounds of the formula III, which in the isomeric ylene form are also termed phosphoranes, for example carbomethoxymethylenetriphenylphosphorane, the negative charge is neutralised by the positively charged phosphonium group. The phosphono compounds of the formula III, which in their isomeric form are also termed phosphonates, are neutralised by a cation of a strong base which, depending on the mode of manufacture, can be, for example, an alkali metal ion, such as a potassium, sodium or lithium ion. The phosphonates are employed in the reaction in this form, that is to say as salts.

The condensation reaction according to the invention is carried out in a suitable inert solvent, for example in an aliphatic, cycloaliphatic or aromatic hydrocarbon, such as hexane, cyclohexane, benzene or toluene, a halogenated hydrocarbon, such as methylene chloride, an ether, such as a di-lower alkyl ether, for example diethyl ether, a di-lower alkoxy-lower alkane, such as dimethoxyethane, a cyclic ether, such as dioxane or tetrahydrofurane, a di-lower alkylamide, such as dimethylformamide, a di-lower alkylsulphoxide, such as dimethylsulphoxide, or a lower alkanol, for example methanol, ethanol or tert.-butanol, or in a mixture thereof, preferably at elevated temperature, such as at about 50° to 150° C., and preferably at about 60° to 100°

C., and if desired, in an inert gas atmosphere, such as a nitrogen atmosphere.

In the reaction according to the invention it is possible, depending on the starting material and the reaction conditions, to obtain single compounds of the formula IA or IB or mixtures of compounds of the formula IA and IB. Resulting mixtures can be separated in a manner which is in itself known, for example with the aid of suitable methods of separation, for example by adsorption and fractional elution, including chromatography (column, paper or plate chromatography) using suitable adsorbents, such as silica gel or aluminium oxide, and eluants, and also by fractional crystallisation, solvent partition and the like.

In the process according to the invention, and in additional measures which may require to be carried out, it is possible, if necessary, temporarily to protect, in a manner which is in itself known, free functional groups, which do not participate in the reaction, in the starting substances or in compounds obtainable according to the process, for example free amino groups by, for example, acylation, tritylation or silylation, free hydroxyl or mercapto groups by, for example, etherification or esterification and free carboxyl groups by, for example, esterification, including silylation, and in each case to liberate them after the reaction has taken place, if desired, individually or conjointly, in a manner which is in itself known. Thus, it is preferably possible, for example, to protect amino, hydroxyl, carboxyl or sulpho groups in an acyl radical $R_1^A$ or $R_1^b$, for example in the form of acylamino groups, such as those mentioned above, for example 2,2,2-trichloroethoxycarbonylamino, 2-bromoethoxycarbonylamino, 4-methoxybenzyloxycarbonylamino, diphenylmethoxycarbonylamino or tert.-butoxycarbonylamino groups, of arylthioamino or aryl-lower alkylthioamino groups, for example 2-nitrophenylthioamino groups, or arylsulphonylamino groups, for example 4-methylphenylsulphonylamino groups, or of 1-lower alkoxycarbonyl-2-propylideneamino groups, or, respectively, of acyloxy groups, such as those mentioned above, for example tert.-butoxycarbonyloxy, 2,2,2-trichloroethoxycarbonyloxy or 2-bromoethoxycarbonyloxy groups, or, respectively, of esterified carboxyl groups, such as those mentioned above, for example diphenylmethoxycarbonyl groups, or, respectively, substituted sulpho groups, such as those mentioned above, for example lower alkylsulpho groups, for example methylsulpho groups, and subsequently, if appropriate after conversion of the protective group, to split, if desired, for example partially, for example a 2,2,2-trichloroethoxycarbonylamino group or 2-iodoethoxycarbonylamino group, or also a p-nitrobenzyloxycarbonylamino group, by treatment with suitable reducing agents, such as zinc in the presence of aqueous acetic acid, a diphenylmethoxycarbonylamino group or tert.-butoxycarbonylamino group by treatment with formic acid or trifluoroacetic acid, an arylthioamino group or aryl-lower alkylthioamino group by treatment with a nucleophilic reagent, such as sulphurous acid, an arylsulphonylamino group by means of electrolytic reduction, a 1-lower alkoxycarbonyl-2-propylideneamino group by treatment with an aqueous mineral acid, or a tert.-butoxycarbonyloxy group by treatment with formic acid or trifluoroacetic acid or a 2,2,2-trichloroethoxycarbonyloxy group or p-nitrobenzyloxycarbonyloxy group by treatment with a chemical reducing agent, such as zinc in the presence of aqueous acetic acid, or a diphenylmethoxycarbonyl group by treatment with formic acid or trifluoroacetic acid, or by hydrogenolysis, or a substituted sulpho group by treatment with an alkali metal halide.

In a compound of the formula IA or IB which is obtainable according to the invention and has a protected, especially an esterified, carboxyl group of the formula $—C(=O)—R_2^A$, the latter can be converted into a free carboxyl group in a manner which is in itself known, for example in accordance with the nature of the group $R_2^A$. An esterified carboxyl group, for example a carboxyl group esterified by a benzyl radical, especially in a 3-carbonylmethylene-cepham compound of the formula IB, can be converted into a free carboxyl group by hydrolysis in a weakly basic medium, for example by treatment with an aqueous solution of an alkali metal hydroxide or carbonate or alkaline earth metal hydroxide or carbonate, for example sodium hydroxide or potassium hydroxide, preferably at a pH value of about 9 to 10 and optionally in the presence of a lower alkanol. A carboxyl group esterified by a suitable 2-halogeno-lower alkyl group, an arylcarbonylmethyl group or a p-nitrobenzyl group can be split, for example, by treatment with a chemical reducing agent, such as a metal, for example zinc, or a reducing metal salt, such as a chromium-II salt, for example chromium-II chloride, usually in the presence of a hydrogen donor, which, together with the metal, is able to produce nascent hydrogen, such as an acid, above all acetic acid, as well as formic acid, or of an alcohol, in which case water is preferably added, a carboxyl group esterified by an arylcarbonylmethyl group can also be split by treatment with a nucleophilic, preferably salt-forming, reagent, such as sodium thiophenolate or sodium iodide, a carboxyl group esterified by a suitable arylmethyl grouping can be split, for example, by irradiation, preferably with ultra-violet light, for example below 290 mµ when the arylmethyl group represents, for example, a benzyl radical which is optionally substituted in the 3-, 4- and/or 5-position, for example by lower alkoxy and-/or nitro groups, or with ultra-violet light of longer wavelength, for example above 290 mµ, when the arylmethyl group denotes, for example, a benzyl radical which is substituted in the 2-position by a nitro group, a carboxyl group esterified by a suitably substituted methyl group, such as tert.-butyl or diphenylmethyl, can be split, for example, by treatment with a suitable acid agent, such as formic acid or trifluoroacetic acid, optionally with the addition of a nucleophilic compound, such as phenol or anisole, an activated esterified carboxyl group can be split by hydrolysis, for example by treatment with an acid or weakly basic aqueous agent, such as hydrochloric acid or aqueous sodium bicarbonate or an aqueous potassium phosphate buffer with a pH of about 7 to about 9, and an esterified carboxyl group which can be split hydrogenolytically can be split by hydrogenolysis, for example by treatment with hydrogen in the presence of a noble metal catalyst, for example a palladium catalyst.

A protected, and especially an esterified, carboxyl group $—C(=O)—R_3$ can be converted into a free carboxyl group in the same way. Depending on the meaning of $R_2^A$ and $R_3$, it is possible either to convert the two protected carboxyl groups $—C(=O)—R_2^A$ and $—C(=O)—R_3$ together into free carboxyl groups or to convert only one of the said protected carboxyl groups into a free carboxyl group. For example, if one of the groups $R_2^A$ or $R_3$ denotes diphenylmethoxy and the other denotes p-nitrobenzyloxy, it is possible either first to split only the diphenylmethoxy group, using trifluoroacetic acid, and then to split the p-nitrobenzyloxy group, using catalytically activated hydrogen, or vice versa.

A carboxyl group protected, for example, by silylation or stannylation can be liberated in the customary manner, for example by treatment with water or an alcohol.

Resulting compounds of the formula IA or IB can be converted into other compounds of the formula IA or IB in a manner which is in itself known.

In a resulting compound, an amino protective group $R_1{}^a$ or $R_1{}^b$, especially an acyl group which can be split off easily, can, for example, be split off in a manner which is in itself known, for example an α-polybranched lower alkoxycarbonyl group, such as tert.-butoxycarbonyl, can be split off by treatment with trifluoroacetic acid and a 2-halogenolower alkoxycarbonyl group, such as 2,2,2-trichloroethoxycarbonyl or 2-iodoethoxycarbonyl, or a phenacyloxycarbonyl group, can be split off by treatment with a suitable reducing metal or corresponding metal compound, for example zinc or a chromium-II compound, such as chromium-II chloride or chromium-II acetate, advantageously in the presence of an agent which, together with the metal or the metal compound, produces nascent hydrogen, and preferably in the presence of aqueous acetic acid.

Furthermore, it is possible, in a resulting compound of the formula IA or IB, wherein a carboxyl group of the formula —C(=O)—$R_2$ or —C(=O)—$R_3$ preferably represents a carboxyl group which is protected, for example by esterification, including by silylation, for example by reaction with a suitable organic halogenosilicon or halogeno-tin-IV compound, such as trimethylchlorosilane or tri-n-butyl-tin chloride, to split off an acyl group $R_1{}^a$ or $R_1{}^b$, wherein any free functional groups which may be present are optionally protected, by treatment with an imide-halide-forming agent, reaction of the resulting imide-halide with an alcohol and splitting of the imino-ether formed, it being possible for a protected carboxyl group, for example a carboxyl group protected by an organic silyl radical, already to be liberated in the course of the reaction.

Imide-halide-forming agents in which halogen is bonded to an electrophilic central atom are, above all, acid halides, such as acid bromides and especially acid chlorides. The acid halides are, above all, acid halides of inorganic acids, above all of phosphorus-containing acids, such as phosphorus oxyhalides, phosphorus trihalides and especially phosphorus pentahalides, for example phosphorus oxychloride, phosphorus trichloride and, above all, phosphorus pentachloride, and also pyrocatechol-phosphorus trichloride, as well as acid halides, especially acid chlorides, of sulphur-containing acids or of carboxylic acids, such as thionyl chloride, phosgene or oxalyl chloride.

The reaction with one of the imide-halide-forming agents mentioned is usually carried out in the presence of a suitable base, especially of an organic base and above all of a tertiary amine, for example a tertiary aliphatic monoamine or diamine, such as a tri-lower alkylamine, for example trimethylamine, triethylamine or N,N-diisopropyl-N-ethylamine, and also of a N,N,N',N'-tetra-lower alkyl-lower alkylenediamine, for example N,N,N',N'-tetramethyl-1,5-pentylenediamine or N,N,N',N'-tetramethyl-1,6-hexylenediamine, of a monocyclic or bicyclic monoamine or diamine, such as a N-substituted, for example N-lower alkylated, alkyleneamine, azaalkyleneamine or oxaalkyleneamine, for example N-methylpiperidine or N-methylmorpholine, and also 2,3,4,6,7,8-hexahydro-pyrrolo[1,2-a]pyrimidine (diazabicyclononene; DBN), or of a tertiary aromatic amine, such as a di-lower alkylaniline, for example N,N-dimethylaniline, or, above all, of a tertiary heterocyclic, monocyclic or bicyclic base, such as quinoline or isoquinoline, and especially pyridine, preferably in the presence of a solvent, such as an optionally halogenated, for example chlorinated, aliphatic or aromatic hydrocarbon, for example methylene chloride. It is possible to use approximately equimolar amounts of the imidehalide-forming agent and of the base; however, the latter can also be present in more than or less than the equivalent amount, for example in an about 0.2-fold to about 1-fold amount or in an approximately up to 10-fold, especially an approximately 3-fold to 5-fold, excess.

The reaction with the imide-halide-forming agent is preferably carried out with cooling, for example at temperatures of from about −50° C. to about +10° C., but it is also possible to work at higher temperatures, that is to say, for example, up to about 75° C., if the stability of the starting materials and of the products permits an elevated temperature.

The imide-halide product, which is usually further processed without isolation, is reacted, according to the process, with an alcohol, preferably in the presence of one of the abovementioned bases, to give the imino-ether. Examples of suitable alcohols are aliphatic as well as araliphatic alcohols, above all optionally substituted, such as halogenated, for example chlorinated, lower alkanols or lower alkanols which contain additional hydroxyl groups, for example ethanol, propanol or butanol, but especially methanol, and also 2-halogeno-lower alkanols, for example 2,2,2-trichloroethanol or 2-bromoethanol, as well as optionally substituted phenyl-lower alkanols, such as benzyl alcohol. Usually an excess, for example an up to about 100-fold excess, of the alcohol is used and the reaction is preferably carried out with cooling, for example at temperatures of from about −50° C. to about 10° C.

The imino-ether product can advantageously be subjected to splitting without isolation. Splitting of the imino-ether can be achieved by treatment with a suitable hydroxy compound, preferably by means of hydrolysis, and also by alcoholysis, and the latter can take place directly following the formation of the imino-ether, if an excess of the alcohol is used. Preferably, water or an alcohol, especially a lower alkanol, for example methanol, or an aqueous mixture of an organic solvent, such as an alcohol, is used. The reaction is usually carried out in an acid medium, for example at a pH value of about 1 to about 5, which can, if necessary, be obtained by adding a basic agent, such as an aqueous alkali metal hydroxide, for example sodium hydroxide or potassium hydroxide, or an acid, for example a mineral acid or an organic acid, such as hydrochloric acid, sulphuric acid, phosphoric acid, fluoboric acid, trifluoroacetic acid or p-toluenesulphonic acid.

The three-stage process described above for splitting off an acyl group is advantageously carried out without isolation of the imide-halide and imino-ether intermediate products, usually in the presence of an organic solvent which is inert with respect to the reactants, such as an optionally halogenated hydrocarbon, for example methylene chloride, and/or in an inert gas atmosphere, such as a nitrogen atmosphere.

The phenoxyacetyl group may be mentioned as an example of an acyl group $R_1^b$ which can be split off easily. Thus, in a compound of the formula IA or IB, wherein $R_1^a$ is hydrogen, the group —CO—$R_2$ is a protected carboxyl group, for example a diphenylmethoxycarbonyl group, and the group —CO—$R_3$ is a functional derivative of a carboxyl group, for example a methoxycarbonyl group, and $R_1^b$ is phenoxyacetyl, it is possible, by the process described above, selectively to split off this phenoxyacetyl group by treatment with $PCl_5$ in methylene chloride in the presence of pyridine and subsequent treatment with methanol, a compound of the formula IA or IB wherein $R_1^a$ and $R_1^b$ represent hydrogen being obtained.

If, on the other hand, the imide-halide intermediate product obtainable according to the above process is reacted, instead of with an alcohol, such as methanol, with a salt, such as an alkali metal salt of a carboxylic acid, especially of a sterically hindered carboxylic acid, a compound of the formula IA or IB, wherein the radical $R_1^a$ represents the newly introduced acyl group and $R_1^b$ represents the acyl group originally present is obtained.

In a compound of the formula IA or IB wherein both of the radicals $R_1^a$ and $R_1^b$ represent acyl groups, one of these groups, preferably the sterically less hindered group, can be removed selectively, for example by hydrolysis or aminolysis.

In a compound of the formulae IA or IB, wherein $R_1^A$ and $R_1^b$, together with the nitrogen atom, represent a phthalimido group, the latter can be converted into a free amino group, for example by hydrazinolysis, that is to say on treatment of such a compound with hydrazine.

Certain acyl radicals $R_1^A$ of an acylamino grouping in compounds obtainable according to the invention, such as, for example, the 5-amino-5-carboxy-valeryl radical, wherein carboxyl is optionally protected, for example by esterification, especially by diphenylmethyl, and/or the amino group is optionally protected, for example by acylation, especially by an acyl radical of an organic carboxylic acid, such as halogeno-lower alkanoyl, such as dichloroacetyl, or phthaloyl, can also be split off by treatment with a nitrosylating agent, such as nitrosyl chloride, with a carbocyclic arenediazonium salt, such as benzenediazonium chloride, or with an agent which releases positive halogen, such as a N-halogeno-amide or N-halogeno-imide, for example N-bromosuccinimide, preferably in a suitable solvent or solvent mixture, such as formic acid, together with a nitro-lower alkane or cyano-lower alkane, and treatment of the reaction product with a hydroxylic agent, such as water or a lower alkanol, for example methanol, or, if, in the 5-amino-5-carboxy-valeryl radical $R_1^A$, the amino group is substituted and the carboxyl group is protected, for example by esterification, and $R_1^b$ preferably represents an acyl radical but can also denote hydrogen, by leaving the substance to stand in an inert solvent, such as dioxane or a halogenated aliphatic hydrocarbon, for example methylene chloride, and, if necessary, working up the free or monoacylated amino compound according to methods which are in themselves known.

A formyl group $R_1^A$ can also be split off by treatment with an acid agent, for example p-toluenesulphonic acid or hydrochloric acid, a weakly basic agent, for example dilute ammonia, or a decarbonylating agent, for example tris-(triphenylphosphine)-rhodium chloride.

A triarylmethyl group $R_1^A$, such as the trityl group $R_1^A$, can be split off, for example, by treatment with an acid agent, such as a mineral acid, for example hydrochloric acid.

In a compound of the formula IA or IB, wherein $R_1^a$ and $R_1^b$ represent hydrogen, the free amino group can be substituted according to methods which are in themselves known and above all can be acylated by treatment with acids, such as a carboxylic acid, or reactive derivatives thereof.

If a free acid, in which any functional groups which may be present, such as an amino group which may be present, are preferably protected, is employed for the acylation, suitable condensing agents, such as carbodiimides, for example N,N'-diethyl-, N,N'-dipropyl-, N,N'-diisopropyl-, N,N'-dicyclohexyl- or N-ethyl-N'-3-dimethylaminopropylcarbodiimide, suitable carbonyl compounds, for example carbonyldiimidazole, or isoxazolinium salts, for example N-ethyl-5-phenyl-isoxazolinium 3'-sulphonate and N-tert.-butyl-5-methylisoxazolinium perchlorate, or a suitable acylamino compound, for example 2-ethoxy-1-ethoxycarbonyl-1,2-dihydroquinoline, are customarily used.

The condensation reaction is preferably carried out in one of the anhydrous reaction media mentioned further below, for example in methylene chloride, dimethylformamide or acetonitrile.

The reaction of a compound of the formula IA or IB, wherein $R_1^a$ and $R_1^b$ represent hydrogen and the groups —$COR_2$ and —$COR_3$ are functional derivatives of carboxyl groups, such as, for example, diphenylmethoxycarbonyl groups and methoxycarbonyl groups, with a carboxylic acid, for example 5-(tert.-butoxycarbonylaminomethyl)-2-thienylacetic acid, and with dicyclohexylcarbodiimide in an inert solvent, for example methylene chloride, can serve as an example of this procedure and, in this reaction, a compound of the formula IA or IB, wherein $R_1^a$ is hydrogen and $R_1^b$ is the 5-tert.-butoxycarbonylaminomethyl-2-thienylacetyl group, from which the tert.-butoxycarbonyl group can be split off easily, as described, for example with trifluoroacetic acid, is obtained.

An amide-forming functional derivative of an acid, in which groups which may be present, such as an amino group which may be present, are preferably protected, is, above all, an anhydride of such an acid, including, and preferably, a mixed anhydride. Mixed anhydrides are, for example, those with inorganic acids, especially with hydrogen halide acids, that is to say the corresponding acid halides, for example acid chlorides or acid bromides, and also with hydrazoic acid, that is to say the corresponding acid azides, with a phosphorus-containing acid, for example phosphoric acid or phosphorous acid, with a sulphur-containing acid, for example sulphuric acid, or with hydrocyanic acid. Further mixed anhydrides are, for example, those with organic acids, such as organic carboxylic acids, such as with lower alkane-carboxylic acids which are optionally substituted, for example by halogen, such as fluorine or chlorine, for example pivalic acid or trichloroacetic acid, or with half-esters, especially lower alkyl half-esters, of carbonic acid, such as the ethyl or isobutyl half-ester of carbonic acid, or with organic, especially aliphatic or aromatic sulphonic acids, for example p-toluenesulphonic acid.

It is also possible to use, as acylating agents, inner anhydrides, such as ketenes, for example diketene, isocyanates (that is to say inner anhydrides of carbamic acid compounds) or inner anhydrides of carboxylic acid compounds having carboxyl-substituted hydroxyl or amino groups, such as mandelic acid O-carboxanhydride or the anhydride of 1-N-carboxyamino-cyclohexanecarboxylic acid.

Further acid derivatives which are suitable for reaction with the free amino group are carboxylic acid derivatives, such as optionally substituted activated esters, such as esters with enols, such as lower alkenols, or phenols, such as phenyl esters, which are preferably substituted by nitro or by halogen, such as chlorine, for example pentachlorophenyl, 4-nitrophenyl or 2,4-dinitrophenyl esters.

Further acylation derivatives are, for example, substituted formimino derivatives, such as substituted N,N-dimethylchloroformimino derivatives of acids, or N-substituted N,N-diacylamines, such as a N,N-diacylated aniline.

The acylation with an acid derivative, such as an anhydride, and especially with an acid halide, can be carried out in the presence of an acid-binding agent, for example of an organic base, such as an organic amine, for example a tertiary amine, such as a tri-lower alkylamine, for example triethylamine, a N,N-di-lower alkylaniline, for example N,N-dimethylaniline, or a base of the pyridine type, for example pyridine, of an inorganic base, for example an alkali metal hydroxide, carbonate or bicarbonate or an alkaline earth metal hydroxide, carbonate or bicarbonate, for example sodium hydroxide, carbonate or bicarbonate, potassium hydroxide, carbonate or bicarbonate or calcium hydroxide, carbonate or bicarbonate, or of an oxirane, for example a lower 1,2-alkylene oxide, such as ethylene oxide or propylene oxide.

The above acylation can be carried out in an aqueous or, preferably, non-aqueous solvent or solvent mixture, for example in a carboxylic acid amide, such as a N,N-di-lower alkylamide, for example dimethylformamide, a halogenated hydrocarbon, for example methylene chloride, carbon tetrachloride or chlorobenzene, a ketone, for example acetone, an ester, for example ethyl acetate, or a nitrile, for example acetonitrile, or mixtures thereof, and, if necessary, at lowered or elevated temperature and/or in an inert gas atmosphere, for example a nitrogen atmosphere.

In the above N-acylation reactions it is possible to start from compounds of the formulae IA or IB, wherein $R_3$ and $R_2$ have the above meaning, and compounds having free carboxyl groups of the formula —C(=O)—$R_2$ and/or —C(=O)—$R_3$, wherein $R_2$ or $R_3$ represents hydroxyl, can also be used in the form of salts, for example ammonium salts, such as with triethylamine, or in the form of a compound with a carboxyl group protected by reaction with a suitable organic phosphorus halide compound, such as with a lower alkyl- or lower alkoxy-phosphorus dihalide, such as methyl-phosphorus dichloride, ethyl-phosphorus dibromide or methoxy-phosphorus dichloride; in the resulting acylation product, the protected carboxyl group can be liberated in a manner which is in itself known, for example as described above, including by hydrolysis or alcoholysis.

An acyl group can also be introduced by acylating a compound of the formula IA or IB, wherein $R_1{}^a$ and $R_1{}^b$ together represent an ylidene radical (which can also be introduced subsequently, for example by treatment of a compound wherein $R_1{}^a$ and $R_1{}^b$ represent hydrogen with an aldehyde, such as an aliphatic, aromatic or araliphatic aldehyde), for example according to the methods indicated above, and the acylation product can be hydrolysed, preferably in a neutral or weakly acid medium.

An acyl group can also be introduced stepwise. Thus, for example, it is possible to introduce into a compound of the formula IA or IB, having a free amino group, a halogeno-lower alkanoyl group, for example a bromoacetyl group, or, for example by treatment with a carbonic acid dihalide, such as phosgene, a halogenocarbonyl group, for example a chlorocarbonyl group, and to react a N-(halogenolower alkanoyl)-amino compound or N-(halogenocarbonyl)-amino compound thus obtainable with suitable exchange reagents, such as basic compounds, for example tetrazole, thio compounds, for example 2-mercapto-1-methyl-imidazole, or metal salts, for example sodium azide, or alcohols, such as lower alkanols, for example tert.-butanol, and thus to obtain substituted N-lower alkanoyl-amino or N-hydroxycarbonylamino compounds.

In both reactants, free functional groups can temporarily be protected during the acylation reaction, in a manner which is in itself known, and can be liberated, after the acylation, by means of methods which are in themselves known, for example as described above.

The acylation can also be effected by replacement of an already existing acyl group by another, preferably sterically hindered, acyl group, for example according to the process described above, by preparing the imidehalide compound, treating this with a salt of an acid and splitting off hydrolytically one of the acyl groups present in the product thus obtainable, usually the sterically less hindered acyl group.

It is furthermore possible, for example, to react a compound of the formula IA or IB, wherein $R_1{}^a$ represents a glycyl group which is preferably substituted in the α-position, such as phenylglycyl, and $R_1{}^b$ represents hydrogen, with an aldehyde, for example formaldehyde, or a ketone, such as a lower alkanone, for example acetone, and thus to obtain compounds of the formula IA or IB wherein $R_1{}^a$ and $R_1{}^b$, together with the nitrogen atom, represent a 5-oxo-1,3-diaza-cyclopentyl radical which is preferably substituted in the 4-position and optionally substituted in the 2-position.

In a compound of the formula IA or IB, wherein $R_1{}^a$ and $R_1{}^b$ represent hydrogen, the free amino group can also be protected by introducing a triarylmethyl group, for example by treatment with a reactive ester of a triarylmethanol, such as trityl chloride, preferably in the presence of a basic agent, such as pyridine.

An amino group can also be protected by introducing a silyl and stannyl group. Such groups are introduced in a manner which is in itself known, for example by treatment with a suitable silylating agent, such as with a dihalogeno-di-lower alkyl-silane, lower alkoxy-lower alkyl-dihalogeno-silane or tri-lower alkyl-silyl halide, for example dichlorodimethylsilane, methoxy-methyldichlorosilane, trimethylsilyl chloride or dimethyl-tert.-butyl-silyl chloride, such silyl halide compounds preferably being used in the presence of a base, for example pyridine, or by treatment with an optionally N-monolower alkylated, N,N-di-lower alkylated, N-tri-lower alkyl-silated or N-lower alkyl-N-tri-lower alkylsilylated N-(tri-lower alkylsilyl)-amine (see, for example, British Pat. No. 1,073,530), or with a silylated carboxylic acid amide, such as a bis-tri-lower alkylsilyl-acetamide, for example bis-trimethyl-silyl acetamide, or trifluorosilylacetamide, and also by treatment with a suitable stannylating agent, such as a bis-(tri-lower alkyl-tin) oxide, for example bis-(tri-n-butyl-tin) oxide, a tri-lower alkyl-tin hydroxide, for example triethyl-tin hydroxide, a tri-lower alkyl-lower alkoxy-tin compound, tetra-lower alkoxy-tin compound or tetra-lower alkyl-tin compound, or with a tri-lower alkyl-tin halide, for example tri-n-butyl-tin chloride (see, for example, Netherlands Published Specification No. 67/11,107).

In a compound of the formula IA or IB which is obtainable according to the process and which contains a free carboxyl group of the formula $-C(=O)-R_2$, such a group can be converted into a protected carboxyl group in a manner which is in itself known. Thus, esters are obtained, for example, by treatment with a suitable diazo compound, such as a diazo-lower alkane, for example diazomethane or diazobutane, or a phenyldiazo-lower alkane, for example diphenyldiazomethane, if necessary in the presence of a Lewis acid, such as, for example, boron trifluoride, or by reaction with an alcohol suitable for esterification, in the presence of an esterifying agent, such as a carbodiimide, for example dicyclohexylcarbodiimide, as well as carbonyldiimidazole, and also with a N,N'-di-substituted O- or S- substituted isourea or isothiourea, wherein an O-substituent and S-substituent are, for example, lower alkyl, especially tert.-butyl, phenyl-lower alkyl or cycloalkyl, and N-substituents or N'-substituents are, for example, lower alkyl, especially isopropyl, cycloalkyl or phenyl, or according to any other known and suitable esterification process, such as reaction of a salt of the acid with a reactive ester of an alcohol and a strong inorganic acid, or with a strong organic sulphonic acid. Furthermore, acid halides, such as acid chlorides (prepared, for example, by treatment with oxalyl chloride), activated esters (formed, for example, with a N-hydroxy-nitrogen compound, such as N-hydroxysuccinimide) or mixed anhydrides (obtained, for example, with lower alkyl halogenoformates, such as ethyl chloroformate or isobutyl chloroformate, or with halogenoacetic acid halides, such as trichloroacetyl chloride) can be converted into an esterified carboxyl group by reaction with alcohols, optionally in the presence of a base, such as pyridine.

In a resulting compound which has an esterified grouping of the formula $-C(=O)-R_2^A$, this grouping can be converted into a different esterified carboxyl group of this formula, for example 2-chloroethoxycarbonyl or 2-bromoethoxycarbonyl can be converted into 2-iodoethoxycarbonyl by treatment with an iodine salt, such as sodium iodide, in the presence of a suitable solvent, such as acetone.

In a compound, obtainable according to the process, which has a free carboxyl group of the formula $-C(=O)-R_2$, such a group can also be converted into an optionally substituted hydrazinocarbonyl group, for which preferably reactive functionally modified derivatives, such as the abovementioned acid halides, and generally esters, such as also the abovementioned activated esters, or mixed anhydrides of the corresponding acid are reacted with hydrazines.

A carboxyl group protected by an organic silyl or stannyl group can be formed in a manner which is in itself known, for example by treating compounds of the formula IA or IB, wherein $R_2$ represents hydroxyl, or salts thereof, such as alkali metal salts thereof, for example sodium salts thereof, with a suitable silylating or stannylating agent, such as one of the abovementioned silylating or stannylating agents; see, for example, British Pat. No. 1,073,530 or Netherlands Published Specification No. 67/17,107.

A free carboxyl group $-C(=O)-R_3$ can be esterified or otherwise converted, for example amidised, in the same way as the free carboxyl group $-C(=O)-R_2^A$.

An esterified carboxyl group $-C(=O)-R_3$ is also formed, for example, when a free carboxyl group is treated with a lower alkyl halogenoformate, such as a lower alkyl chloroformate, in the presence of a base, the mixed anhydride which is first formed as an intermediate product being decarboxylated.

In a compound, obtainable according to the process, which has a free carboxyl group $-C(=O)-R_3$, such a group can be converted into an optionally substituted amide group, for which preferably reactive functionally modified derivatives, such as the abovementioned acid halides, esters, and especially also the abovementioned activated esters, or mixed anhydrides of the corresponding acid are reacted with ammonia or optionally substituted amines, for example with a di-lower alkylamine, such as diethylamine, aromatic amines, such as aniline, heterocyclic amines, such as pyrrolidine or morpholine, or with a corresponding hydrazine, such as hydrazine, phenylhydrazine or 4-methylpiperazine-1-ylamine, or with an aminocarboxylic acid in which the functional groups which are not to be reacted are preferably protected, for example the tert.-butyl ester of $N_\alpha$-tert.-butoxycarbonyl-lysine, or with a heterocyclylamine, for example 2-methyl-5-amino-thiadiazole.

If, when producing an amidised carboxyl group $-COR_3$, the free carboxylic acids, wherein $R_3$ denotes hydroxyl, are used in place of the abovementioned reactive functionally modified derivatives which are preferably used, the amidisation can be carried out with equivalent to excess amounts of amine in the presence of preferably equivalent amounts of a condensing agent, such as cyclohexylcarbodiimide, in an inert solvent, such as those mentioned above, for example in tetrahydrofurane or benzene, or in mixtures thereof. For this reaction, the diverse amines mentioned above, for example ammonia, aniline, 2-methyl-5-amino-thiadiazole or an aminocarboxylic acid in which the reactive groups which are not to be reacted are protected, such as, for example, the tert.-butyl ester of $N_\alpha$-tert.-butoxycarbonyl-lysine, can be used.

It is furthermore possible to liberate modified functional substituents in groups $R_1^A$, $R_1^b$, $R_2$ and/or $R_3$, such as substituted amino groups, acylated hydroxyl groups, esterified carboxyl groups or substituted sulpho groups, according to methods which are in themselves known, for example those described above, or functionally to modify free functional substituents in groups $R_1^A$, $R_1^b$ and $R_2$ and/or $R_3$, such as free amino, hydroxyl, carboxyl or sulpho groups, according to processes which are in themselves known, for example acylation or esterification or substitution. Thus, for example, an amino group can be converted into a sulphoamino group by treatment with sulphur trioxide, preferably in the form of a complex with an organic base, such as a tri-lower alkylamine, for example triethylamine. Furthermore, the reaction mixture obtained by reaction of an acid addition salt of a 4-guanyl-semicarbazide with sodium mitrite can be reacted with a compound of the formula IA or IB wherein, for example, the amino protective group $R_1^A$ represents an optionally substituted glycyl group, and the amino group can thus be converted into a 3-guanylureido group. Furthermore, compounds with aliphatically bonded halogen, for example with an optionally substituted α-bromoacetyl grouping, can be reacted with esters of phosphorous acid, such as tri-lower alkyl phosphite compounds, and corresponding phosphono compounds can thus be obtained.

Resulting cephem compounds of the formula IA and IB can be converted into their 1-oxides by oxidation with suitable oxidising agents, such as those described below. Resulting 1-oxides of 3-cephem compounds of the formula IA can be reduced to the corresponding 3-cephem compounds of the formula IA by reduction with suitable reducing agents, such as, for example, those described below. In these reactions care must be taken to ensure that, if necessary, free functional groups are protected and, if desired, are subsequently liberated again.

Resulting cephem compounds can be isomerised. Thus, resulting 3-carbonylmethylene-cepham compounds of the formula IB, or resulting mixtures of such compounds with 3-cephem compounds, can be converted into the corresponding 3-cephem compounds of the formula IA by isomerising a 3-carbonylmethylene-cepham compound of the formula IB, or a mixture consisting of such a compound and a 3-cephem compound, wherein free functional groups can, if appropriate, be temporarily protected, for example as indicated.

Thus, it is possible to isomerise a 3-carbonylmethylene-cepham compound of the formula IB by treating it with a basic agent and isolating the corresponding 3-cephem compound of the formula IA from an equilibrium mixture which consists of the 3-carbonylmethylene-cepham and the 3-cephem compounds and may be obtained.

Suitable isomerising agents are, for example, organic nitrogen-containing bases, such as tertiary heterocyclic bases of aromatic character, and above all tertiary aliphatic, azacycloaliphatic or araliphatic bases, such as N,N,N-trilower alkylamines, for example N,N,N-trimethylamine, N,N-dimethyl-N-ethylamine, N,N,N-triethylamine or N,N-diisopropyl-N-ethylamine, N-lower alkyl-azacycloalkanes, for example N-methylpiperidine, or N-phenyl-lower alkyl-N,N-di-lower alkylamines, for example N-benzyl-N,N-dimethylamine, as well as mixtures thereof, such as the mixture of a base of the pyridine type, for example pyridine, and a N,N,N-trilower alkylamine, for example the mixture of pyridine and triethylamine. Furthermore, it is also possible to use inorganic or organic salts of bases, especially of medium strength to strong bases, with weak acids, such as alkali metal salts or ammonium salts of lower alkanecarboxylic acids, for example sodium acetate, triethylammonium acetate or N-methylpiperidine acetate, as well as other analogous bases or mixtures of such basic agents.

The above isomerisation with basic can be carried out, for example, in the presence of a derivative of a carboxylic acid which is suitable for forming a mixed anhydride, such as a carboxylic acid anhydride or carboxylic acid halide, for example with pyridine in the presence of acetic anhydride. The reaction is preferably carried out in an anhydrous medium, in the presence or absence of a solvent, such as an optionally halogenated, for example chlorinated, aliphatic, cycloaliphatic or aromatic hydrocarbon, or of a solvent mixture, it being possible for bases which are used as reactants and are liquid under the reaction conditions at the same time also to serve as solvents, and if necessary with cooling or heating, preferably in a temperature range from about $-30°$ C. to about $+100°$ C., in an inert gas atmosphere, for example a nitrogen atmosphere, and/or in a closed vessel.

The 3-cephem compounds of the formula IA, thus obtainable, can be separated from any 3-carbonylmethylene-cepham compounds of the formula IB, which may still be present, in a manner which is in itself known, for example by adsorption and/or crystallisation.

The isomerisation of a 3-carbonylmethylene-cepham compound of the formula IB can also be carried out by oxidising this compound in the 1-position, isomerising a 3-carbonylmethylene-cepham-1-oxide, which may be obtained when the oxidation is carried out in an apolar solvent, such as in an optionally halogenated hydrocarbon, for example chloroform or methylene chloride, or in an etherlike solvent, for example dioxane or tetrahydrofurane, to the 3-cephem-1-oxide by bringing it into contact with a polar solvent such as a di-lower alkylsulphoxide, for example dimethylsulphoxide, a di-lower alkylacylamide, such as dimethylformamide or N,N-dimethylacetamide, or also with a solvent contaning hydroxyl groups, such as an acid, such as a lower alkanecarboxylic acid, for example formic acid or acetic acid, or with an aqueous base, for example aqueous sodium bicarbonate solution, and, if desired, separating a mixture, which may be obtained, of the 3-cephem-1-α-oxide and 3-cephem-1β-oxide isomers and reducing the 1-oxides of the corresponding 3-cephem compound, which are thus obtainable.

Suitable oxidising agents for the oxidation of 3-(carbonylmethylene)-cepham compounds in the 1-position are inorganic per-acids which have a redox potential of at least $+1.5$ volt and which consist of non-metallic elements, or organic per-acids or mixtures of hydrogen peroxide and acids, especially organic carboxylic acids, which have a dissociation constant of at least $10^{-5}$. Suitable inorganic per-acids are periodic acid and persulphuric acid. Organic per-acids are corresponding percarboxylic and persulphonic acids, which can be added as such or can be formed in situ by using at least one equivalent of hydrogen peroxide and of a carboxylic acid. It is appropriate to use a large excess of the carboxylic acid when, for example, acetic acid is used as the solent. Suitable per-acids are, for example, performic acid, peracetic acid, pertrifluoroacetic acid, permaleic acid, perbenzoic acid, monoperphthalic acid or p-toluenepersulphonic acid.

The oxidation can also be carried out using hydrogen peroxide with catalytic amounts of an acid which has a dissociation constant of at least $10^{-5}$ and it is possible to employ low concentrations, for example 1–2% and less, but also larger amounts, of the acid. The activity of the mixture depends, above all, on the strength of the acid. Suitable mixtures are, for example, those of hydrogen peroxide with acetic acid, perchloric acid or trifluoroacetic acid.

The above oxidation can be carried out in the presence of suitable catalysts. Thus, for example, the oxidation with percarboxylic acids can be catalysed by the presence of an acid which has a dissociation constant of at least $10^{-5}$, its activity depending on its strength. Examples of acids which are suitable as catalysts are acetic acid, perchloric acid and trifluoroacetic acid. Usually, at least equimolar amounts of the oxidising agent, and preferably a small excess of about 10% to about 20%, are used: The oxidation is carried out under mild conditions, for example at temperatures of from about −50° C. to about +100° C., and preferably of from about −10° C. to about +40° C.

The oxidation of 3-carbonylmethylene-cepham compounds to the 1-oxides of the corresponding 3-cephem compounds can also be carried out by treatment with organic hypohalite compounds, such as lower alkyl hypochlorites, for example tert.-butyl hypochlorite, which are used in the presence of inert solvents, such as optionally halogenated hydrocarbons, for example methylene chloride, and at temperatures of from about −10° C. to about +30° C., with periodate compounds, such as alkali metal periodates, for example potassium periodate, which are preferably used in an aqueous medium at a pH value of about 6 and at temperatures of from about −10° C. to about +30° C., with iodobenzene dichloride, which is used in an aqueous medium, preferably in the presence of an organic base, for example pyridine, and with cooling, for example at temperatures of from about −20° C. to about 0°, or with any other oxidising agent which is suitable for converting a thio grouping into a sulphoxide grouping.

In the 1-oxides of 3-cephem compounds of the formula IA, which are thus obtainable, and especially in those compounds in which $R_1{}^a$, $R_1{}^b$, $R_2$ and $R_3$ have the preferred meanings indicated above, the groups $R_1{}^a$, $R_1{}^b$, $R_2$ and/or $R_3$ can, within the defined scope, be converted into one another, split off or introduced. A mixture of isomeric $\alpha$- and $\beta$-1-oxides can be separated, for example by chromatography.

The reduction of the 1-oxides of 3-cephem compounds of the formula IA can be carried out in a manner which is in itself known, by treatment with a reducing agent, if necessary in the presence of an activating agent. Reducing agents which can be used are: catalytically activated hydrogen, using noble metal catalysts which contain palladium, platinum or rhodium and which are optionally employed together with a suitable support material, such as charcoal or barium sulphate; reducing tin, iron, copper or manganese cations, which are used in the form of corresponding compounds or complexes of an inorganic or organic nature, for example as tin-II chloride, fluoride, acetate or formate, iron-II chloride, sulphate, oxalate or succinate, copper-I chloride, benzoate or oxide, or manganese-II chloride, sulphate, acetate or oxide, or as complexes, for example with ethylenediaminetetraacetic acid or nitrilotriacetic acid; reducing dithionite, iodide or ferrocyanide anions, which are used in the form of corresponding inorganic or organic salts, such as alkali metal salts, for example sodium dithionite or potassium dithionite, sodium iodide or potassium iodide, or sodium ferrocyanide or potassium ferrocyanide, or in the form of the corresponding acids, such as hydriodic acid; reducing trivalent inorganic or organic phosphorus compounds, such as phosphines, and also esters, amides and halides of phosphinous, phosphonous or phosphorous acid, as well as phosphorus-sulphur compounds corresponding to these phosphorus-oxygen compounds, in which compounds organic radicals above all represent aliphatic, aromatic or araliphatic radicals, for example optionally substituted lower alkyl, phenyl or phenyllower alkyl groups, such as, for example, triphenylphosphine, tri-n-butylphosphine, methyl diphenylphosphinite, diphenylchlorophosphine, phenyldichlorophosphine, dimethyl benzenephosphinite, methyl butanephosphonite, triphenyl phosphite, trimethyl phosphite, phosphorus trichloride, phosphorus tribromide and the like; reducing halogenosilane compounds which possess at least one hydrogen atom bonded to the silicon atom and which, in addition to halogen, such as chlorine, bromine or iodine, can also possess organic radicals, such as aliphatic or aromatic groups, for example optionally substituted lower alkyl or phenyl groups, such as chlorosilane, bromosilane, dichlorosilane or trichlorosilane, dibromosilane or tribromosilane, diphenylchlorosilane, dimethylchlorosilane and the like; reducing quaternary chloromethyleneiminium salts, especially chlorides or bromides, wherein the iminium group is substituted by one divalent organic radical or two monovalent organic radicals, such as optionally substituted lower alkylene or lower alkyl groups, such as N-chloromethylene-N,N-diethyliminium chloride or N-chloromethylenepyrrolidinium chloride; and complex metal hydrides, such as sodium borohydride, in the presence of suitable activating agents, such as cobalt-II chloride, as well as borane dichloride.

Activating agents which may be mentioned and which are used together with those of the abovementioned reducing agents which do not themselves possess Lewis acid properties, that is to say which are employed, above all, together with the dithionite, iodide or ferrocyanide reducing agents and the trivalent phosphorus reducing agents which do not contain halogen, or in the case of catalytic reduction, are, in particular, organic carboxylic acid halides and sulphonic acid halides, as well as sulphur halides, phosphorus halides or silicon halides which have a second order hydrolysis constant equal to, or greater than, that of benzoyl chloride, for example phosgene, oxalyl chloride, acetyl chloride or acetyl bromide, chloroacetyl chloride, pivalyl chloride, 4-methoxybenzoyl chloride, 4-cyanobenzoyl chloride, p-toluenesulphonyl chloride, methanesulphonyl chloride, thionyl chloride, phosphorus oxychloride, phosphorus trichloride, phosphorus tribromide, phenyldichlorophosphine, benzenephosphonous acid dichloride, dimethylchlorosilane or trichlorosilane, and also suitable acid anhydrides, such as trifluoroacetic anhydride, or cyclic sultones, such as ethanesultone, 1,3-propanesulton, 1,4-butanesulton or 1,3-hexanesultone.

The reduction is preferably carried out in the presence of solvents or mixtures thereof, the choice of which is determined, above all, by the solubility of the starting materials and the choice of the reducing agent, and thus, for example, is carried out in the presence of lower alkanecarboxylic acids or esters thereof, such as acetic acid and ethyl acetate, in the case of catalytic reduction and, for example, in the presence of optionally substituted, such as halogenated or nitrated, aliphatic, cycloaliphatic, aromatic or araliphatic hydrocarbons, for example benzene, methylene chloride, chloroform or nitromethane, suitable acid derivatives, such as lower alkanecarboxylic acid esters or nitriles, for example ethyl acetate or acetonitrile, or amides of inorganic or organic acids, for example dimethylformamide, dimethylacetamide or hexamethylphosphoric acid amide, ethers, for example diethyl ether, tetrahydrofurane or dioxane, ketones, for example acetone, or sulphones, especially aliphatic sulphones, for example dimethylsulphone or tetramethylenesulphone, and the like, together with the chemical reducing agents, these solvents preferably not containing any water. The reaction is usually carried out at temperatures of from about −20° C. to about 100° C., it being possible for the reaction to be carried out at lower temperatures when highly reactive activating agents are used.

Salts of compounds of the formulae IA and IB can be manufactured in a manner which is in itself known. Thus, salts of those compounds which possess acid groups can be formed, for example, by treatment with metal compounds, such as alkali metal salts of suitable carboxylic acids, for example the sodium salt of α-ethylcaproic acid, or with ammonia or a suitable organic amine, preferably using stoichiometric amounts or only a small excess of the salt-forming agent. Acid addition salts of compounds of the formulae IA and IB which possess basic groupings are obtained in the customary manner, for example by treatment with an acid or a suitable anion exchange reagent. Inner salts of compounds of the formulae IA and IB which contain a salt-forming amino group and a free carboxyl group can be formed, for example, by neutralising salts, such as acid addition salts, to the isoelectric point, for example with weak bases, or by treatment with liquid ion exchangers. Salts of 1-oxides of compounds of the formula IA which have salt-forming groups can be manufactured in an analogous manner.

Salts can be converted into the free compounds in the customary manner, metal salts and ammonium salts, for example, by treatment with suitable acids and acid addition salts, for example, by treatment with a suitable basic agent.

Resulting mixtures of isomers can be separated into the individual isomers according to methods which are in themselves known; mixtures of diastereomeric isomers, for example, can be separated by fractional crystallisation, adsorption chromatography (column chromatography or thin layer chromatography) or other suitable methods of separation. Resulting racemates can be resolved into the antipodes in the customary manner, if appropriate after introducing suitable salt-forming groupings, for example by forming a mixture of diastereomeric salts with optically active salt-forming agents, separating the mixture into the diastereomeric salts and converting these salts into the free compounds, or by fractional crystallisation from optically active solvents.

The process also comprises those embodiments according to which compounds obtained as intermediate products are used as starting materials and the remaining process steps are carried out with these, or the process is discontinued at any stage; furthermore, starting materials can be used in the form of derivatives or can be formed during the reaction.

Preferably, the starting materials used and the reaction conditions chosen are such that the compounds mentioned initially as being particularly preferred are obtained.

The starting materials of the formula II and III, which are used according to the invention, are known or can be manufactured analogously to known methods.

The pharmacologically usable compounds of the present invention can, for example, be used for the manufacture of pharmaceutical formulations which contain an effective amount of the active substance together with, or mixed with, inorganic or organic, solid or liquid, excipients which can be used pharmaceutically and which are suitable for enteral administration or preferably for parenteral administration. Thus, tablets or gelatine capsules are used which contain the active compound together with diluents, for example lactose, dextrose, sucrose, mannitol, sorbitol, cellulose and/or glycine, and lubricants, for example silica, talc, stearic acid or salts thereof, such as magnesium stearate or calcium stearate, and/or polyethylene glycol; tablets also contain binders, for example magnesium aluminium silicate, starches, such as maize starch, wheat starch, rice starch or arrowroot, gelatine, tragacanth, methylcellulose, sodium carboxymethylcellulose and/or polyvinylpyrrolidone and, if desired, disintegrating agents, for example starches, agar, alginic acid or a salt thereof, such as sodium alginate, and/or effervescent mixtures, or adsorbents, dyestuffs, flavouring substances and sweeteners. Furthermore, the new pharmacologically active compounds can be used in the form of injectable formulations, for example formulations which can be administered intravenously, or of infusion solutions. Such solutions are, preferably, isotonic aqueous solutions or suspensions and these can, for example, be prepared before use from lyophilised formulations which contain the active substance on its own or together with an excipient, for example mannitol. The pharmaceutical formulations can be sterilised and/or contain auxiliaries, for example preservatives, stabilisers, wetting agents and/or emulsifiers, solubilising agents, salts for regulating the osmotic pressure and/or buffers. The present pharmaceutical formulations, which can, if desired, contain further pharmacologically valuable substances, are manufactured in a manner which is in itself known, for example by means of conventional mixing, granulating, dragee-making, dissolving or lyophilising processes, and contain from about 0.1% to 100%, and especially from about 1% to about 50%, of the active compound and lyophilised products contain up to 100% of the active compound.

In the context of the present description, the organic radicals described as "lower" contain, unless expressly defined, up to 7, and preferably up to 4, carbon atoms; acyl radicals contain up to 20, preferably up to 12 and above all up to 7, carbon atoms.

The examples which follow serve to illustrate the invention; temperatures are given in degrees centigrade. The cephem compounds mentioned in the examples possess the R-configuration in the 6-position and 7-position.

EXAMPLE 1

A mixture of 6.15 g (10 mmols) of diphenylmethyl 7β-[D(−)-α-tert.-butoxycarbonylamino-phenylacetylamino]-3-hydroxy-3-cephem-4-carboxylate and 4.0 g (12 mmols) of carbomethoxymethylenetriphenylphosphorane in 100 ml of toluene is warmed to 100° for 1 hour, under nitrogen. The solvent is evaporated off and the residue is chromatographed over 250 g of silica gel. A mixture consisting of diphenylmethyl 3-carbomethoxymethyl-7β-[D(−)-α-tert.-butoxycarbonylamino-phenylacetylamino]-3-cephem-4-carboxylate and diphenylmethyl 3-carbomethoxymethylene-7β-[D(−)-α-tert.-butoxycarbonylamino-phenylacetylamino]-cepham-4-carboxylate is eluted with toluene containing 10 to 20% of ethyl acetate. Thin layer chromatogram: Rf~0.50 (silica gel; toluene/ethyl acetate, 1:1); IR spectrum (CH$_2$Cl$_2$): bands at 2.96, 5.61, 5.76, 5.82 (shoulder), 5.91 and 6.70μ.

The resulting mixture of isomers can be further processed as follows:

(a) 1.63 g (8.3 mmols) of 85 percent strength m-chloroperbenzoic acid are added to a solution of 5.06 g (7.54 mmols) of a mixture of isomers consisting of diphenylmethyl 3-carbomethoxymethyl-7β-[D(−)-α-tert.-butoxycarbonylaminophenylacetylamino]-3-cephem-4-carboxylate and diphenylmethyl 3-carbomethoxymethylene-7β-[D(−)-α-tert.-butoxycarbonylaminophenylacetylamino]-cepham-4-carboxylate in 50 ml of methylene chloride and the mixture is stirred for 2.5 hours in an ice bath. The solvent is removed in vacuo, the residue is taken up in ethyl acetate and the solution is washed successively with a saturated aqueous solution of sodium bicarbonate and a saturated aqueous solution of sodium chloride, dried over sodium sulphate and evaporated in vacuo. The crude product is recrystallised from methylene chloride/diethyl ether and gives the 1-oxide of diphenylmethyl 3-carbomethoxymethyl-7β-[D(−)-α-tert.-butoxycarbonylaminophenylacetylamino]-3-cephem-4-carboxylate, which has a melting point of 220° C.; $[\alpha]_D^{20} = +8° \pm 1°$ (c=1; in dimethylsulphoxide); UV spectrum (in ethanol): $\lambda_{max}=268$ nm ($\epsilon = 8,200$); IR spectrum (in Nujol): bands at 2.94, 3.00, 5.58, 5.78, 5.84, 5.96 (shoulder), 6.02, 6.14 and 6.52μ.

(b) A solution of 2.0 g (2.91 mmols) of the 1-oxide of diphenylmethyl 3-carbomethoxymethyl-7β-[D(−)-α-tert.-butoxycarbonylamino-phenylacetylamino]-3-cephem-4-carboxylate in 20 ml of dimethylformamide is stirred with 0.51 ml (5.82 mmols) of phosphorus trichloride for 15 minutes at −10° C. The reaction mixture is poured onto ice and extracted with ethyl acetate and the organic phase is washed with water, a saturated aqueous solution of sodium bicarbonate and a saturated aqueous solution of sodium chloride, dried over sodium sulphate and evaporated in vacuo. The residue is chromatographed over 60 g of silica gel using toluene/ethyl acetate, 4:1, and gives diphenylmethyl 3-carbomethoxymethyl-7β-[D(−)-α-tert.-butoxycarbonylaminophenylacetylamino]-3-cephem-4-carboxylate, which, when recrystallised from methylene chloride, has a melting point of 170°–172° C.; $[\alpha]_D^{20} = -18° \pm 1°$ (c=1.46; chloroform); UV spectrum (in ethanol): $\lambda_{max}=262$ nm ($\epsilon=7,200$); IR spectrum (in Nujol): bands at 3.00, 5.61, 5.74, 5.85, 5.92; 6.00 and 6.56μ.

(c) 1.09 ml (10 mmols) of anisole and 6.12 ml (80 mmols) of trifluoroacetic acid are added to a solution of 1.33 g (2.0 mmols) of diphenylmethyl 3-carbomethoxymethyl-7β-[D(−)-α-tert.-butoxycarbonylaminophenylacetylamino]-3-cephem-4-carboxylate in 6.5 ml of methylene chloride, the mixture is stirred for 30 minutes in an ice bath, 100 ml of cold toluene are added and the resulting mixture is evaporated in vacuo. The dry residue is digested with diethyl ether and the precipitate is filtered off and dried in vacuo. The resulting trifluoroacetate of 3-carbomethoxymethyl-7β-[D(−)-phenylglycylamino]-3-cephem-4-carboxylic acid is suspended in 5 ml of water and dissolved by adding 3 ml of methanol and the pH value of the solution is adjusted to 4.7 by adding a 10% strength methanolic solution of triethylamine dropwise. The gelatinous mass which has formed is converted, by stirring with acetone and diethyl ether, into a microcrystalline product which can be filtered easily and this, when it is filtered off, washed with acetone and diethyl ether and dried under a high vacuum gives the inner salt of 3-carbomethoxymethyl-7β-[D(−)-phenylglycylamino]-3-cephem-4-carboxylic acid which has a melting point of 140°–143° C. (decomposition). UV spectrum (in 0.1 N hydrochloric acid) $\lambda_{max}=257$ nm ($\epsilon=6,400$); IR spectrum (in Nujol): bands at 2.94, 3.14, 5.64, 5.74, 5.87, 6.17, 6.38 and 6.58μ.

EXAMPLE 2

A mixture of 12.3 g (20 mmols) of diphenylmethyl 7β-[D(−)-α-tert.-butoxycarbonylaminophenylacetylamino]-3-hydroxy-3-cephem-4-carboxylate and 10.9 g (24 mmols) of p-nitro-carbobenzyloxymethylene-triphenylphosphorane in 200 ml of toluene is warmed to 100° for 1 hour, under nitrogen. The solvent is evaporated off and the residue is chromatographed over 700 g of silica gel. A mixture consisting of diphenylmethyl 3-p-nitrocarbobenzyloxymethyl-7β-[D(−)-α-tert.-butoxycarbonylaminophenylacetylamino]-3-cephem-4-carboxylate and diphenylmethyl 3-p-nitrocarbobenzyloxymethylene-7β-[D(−)-α-tert.-butoxycarbonylaminophenylacetylamino]-cepham-4-carboxylate is eluted with toluene/ethyl acetate, 4:1. Thin layer chromatogram: Rf∼0.55 (silica gel; toluene/ethyl acetate, 1:1); IR spectrum (CH$_2$Cl$_2$): bands at 2.94, 5.60, 5.75 (shoulder), 5.81, 6.22, 6.56 and 6.69μ.

The resulting mixture of isomers can be further processed as follows:

(a) 3.27 g (16 mmols) of 85 percent strength m-chloroperbenzoic acid are added to a solution of 11.6 g (14.6 mmols) of a mixture of isomers consisting of diphenylmethyl 3-p-nitrocarbobenzyloxymethyl-7β-[D(−-α-tert.-butoxycarbonylaminophenylacetylamino]-3-cephem-4-carboxylate and diphenylmethyl 3-p-nitrocarbobenzyloxymethylene-7β-[D(−)-α-tert.-butoxycarbonylaminophenylacetylamino]-cepham-4-carboxylate in 230 ml of methylene chloride and the mixture is stirred for 1 hour under nitrogen. The solvent is removed in vacuo, the residue is taken up in ethyl acetate and the solution is washed successively with a saturated aqueous solution of sodium bicarbonate and a saturated aqueous solution of sodium chloride, dried over sodium sulphate and evaporated in vacuo. The crude product is recrystallised from ethyl acetate/hexane and gives the 1-oxide of diphenylmethyl 3-p-nitrocarbobenzyloxymethyl-7β-[D(−)-α-tert.-butoxycarbonylaminophenylacetylamino]-3-cephem-4-carboxylate in a microcrystalline form. Thin layer chromatogram: Rf value∼0.23 (silica gel; toluene/ethyl acetate, 1:1); UV spectrum (in ethanol): $\lambda_{max}=269$ nm ($\epsilon=17,800$); IR spectrum (in Nujol): bands at 3.05, 5.58, 5.77, 5.82 (shoulder), 5.92, 6.02, 6.23 and 6.58μ.

(b) A solution of 6.84 g (8.4 mmols) of the 1-oxide of diphenylmethyl 3-p-nitrocarbobenzyloxymethyl-7β-[D(−)-α-tert.-butoxycarbonylaminophenylacetylamino]-3-cephem-4-carboxylate in 24 ml of dimethylformamide is stirred with 1.48 ml (16.8 mmols) of phosphorus trichloride for 15 minutes at −10° C. The reaction mixture is poured onto ice and extracted with ethyl acetate and the organic phase is washed with water, a saturated aqueous solution of sodium bicarbonate and a saturated aqueous solution of sodium chloride, dried over sodium sulphate and evaporated in vacuo. The residue is chromatographed over 180 g of silica gel using toluene/ethyl acetate, 9:1 and 4:1, and gives diphenylmethyl 3-p-nitrocarbobenzyloxymethyl-7β-[D(−)-α-tert.-butoxycarbonylaminophenylacetylamino]-3-cephem-4-carboxylate; thin layer chromatogram: Rf value∼0.55 (silica gel; toluene/ethyl acetate, 1:1); UV spectrum (in ethanol): $\lambda_{max}=264$ nm ($\epsilon=16,200$); IR spectrum (in Nujol): bands at 3.04, 5.60, 5.75 (shoulder), 5.81, 5.92, 6.23, 6.58 and 6.68μ.

(c) 1.09 ml (~10 mmols) of anisole and 6.18 ml (80 mmols) of trifluoroacetic acid are added to a solution of 1.59 g (~2.0 mmols) of diphenylmethyl 3-p-nitrocarbobenzyloxymethyl-7$\beta$-[D(—)-$\alpha$-tert.-butoxycarbonylamino-phenylacetylamino]-3-cephem-4-carboxylate in 12.5 ml of methylene chloride, the mixture is stirred for 30 minutes under nitrogen in an ice bath, 50 ml of cold toluene are added and the resulting mixture is evaporated in vacuo. The dry residue is digested with diethyl ether and the precipitate is filtered off, washed with diethyl ether and dried in vacuo. The resulting trifluoroacetate of 3-p-nitrocarbobenzyloxymethyl-7$\beta$-[D(—-phenylglycylamino)-3-cephem-4-carboxylic acid is dissolved in 15 ml of 2:1 water/methanol, the small amount of insoluble material is filtered off and the pH value of the solution is adjusted to about 4.5 by adding a 10% strength methanolic solution of triethylamine dropwise. The precipitate is filtered off, washed with methylene chloride and diethyl ether and dried under a high vacuum and gives the inner salt of 3-p-nitrocarbobenzyloxymethyl-7$\beta$-[D(—)-phenylglycylamino)-3-cephem-4-carboxylic acid; thin layer chromatogram: Rf value ~0.42 (silica gel; n-butanol/acetatic acid/water, 67:10:23); UV spectrum (in 0.1 N hydrochloric acid) $\lambda_{max}$=267 nm ($\epsilon$=1,300); IR spectrum (in Nujol): bands at 2.85, 3.03 (shoulder), 5.66, 5.75 (shoulder), 5.92, 6.22 and 6.58$\mu$.

(d) A solution of 0.793 g (1.0 mmol) of diphenylmethyl 3-p-nitrocarbobenzyloxymethyl-7$\beta$-[D(—)-$\alpha$-tert.-butoxycarbonylamino-phenylacetylamino]-3-cephem-4-carboxylate in 50 ml of methanol is hydrogenated with 790 mg of a 5% strength palladium-on-charcoal catalyst for 8 hours at room temperature and under normal pressure. After filtering off the catalyst, the hydrogenation solution is evaporated in vacuo and the residue is chromatographed over 20 g of silica gel (deactivated with 0.5 ml of water). Elution with methylene chloride containing increasing proportions of ethyl acetate gives diphenylmethyl 3-carboxymethyl-7$\beta$-[D(—)-$\alpha$-tert.-butoxycarbonylamino-phenylacetylamino]-3-cephem-4-carboxylate; thin layer chromatogram; Rf value ~0.12 (silica gel; chloroform/methanol, 95:5); UV spectrum (in ethanol): $\lambda_{max}$=257 nm ($\epsilon$=6,800); IR spectrum (in methylene chloride): bands at 2.96, 5.60, 5.82, 5.88 (shoulder) and 6.69$\mu$.

(e) 0.27 ml (2.5 mmols) of anisole and 1.55 ml (20 mmols) of trifluoroacetic acid are added to a solution of 329 mg (0.5 mmol) of diphenylmethyl 3-carboxymethyl-7$\beta$-[D(—)-$\alpha$-tert.-butoxycarbonylamino-phenylglycylamino]-3-cephem-4-carboxylate in 3.5 ml of methylene chloride, the mixture is stirred for 30 minutes under nitrogen in an ice bath, 15 ml of cold toluene are added and the resulting mixture is evaporated in vacuo. The dry residue is digested with diethyl ether and the precipitate is filtered off, washed with diethyl ether and dried in vacuo. The resulting trifluoroacetate of 3-carboxymethyl-7$\beta$-[D(—)-phenylglycyloamino]-3-cephem-4-carboxylic acid is dissolved in a small amount of 1:1 methanol/water and the pH value of the solution is adjusted to 4.7 by adding a 10% strength methanolic solution of triethylamine dropwise. The crude product is precipitated by stirring with acetone and diethyl ether, filtered off, washed with acetone, methylene chloride and diethyl ether and dried under a high vacuum and gives the inner salt of 3-carboxymethyl-7$\beta$-[D(—)-phenylglycylamino]-3-cephem-4-carboxylic acid; thin layer chromatogram: Rf value ~0.32 (silica gel; n-butanol/pyridine/acetic acid/water, 40:24:6:30; UV spectrum (in 0.1 N hydrochloric acid) $\lambda_{max}$=258 nm ($\epsilon$=6,500); IR spectrum (in Nujol): bands at 2.94, 3.14, 5.64, 5.74, 5.87, 6.17, 6.38 and 6.58$\mu$.

(f) 0.26 ml (3 mmols) of oxalyl chloride and 2 drops of dimethylformamide are added to a solution of 0.987 g (1.5 mmols) of diphenylmethyl 3-carboxymethyl-7$\beta$-[D(—)-$\alpha$-tert.-butoxycarbonylamino-phenylacetylamino]-3-cephem-4-carboxylate in 60 ml of benzene and the mixture is stirred for 45 minutes at 6° to 8° C. and then concentrated in vacuo. The residue is taken up in 60 ml of benzene and 0.13 ml (1.5 mmols) of pyridine and 0.16 ml (1.5 mmols) of diethylamine are added and the mixture is stirred for 3.5 hours at room temperature. The reaction mixture is diluted with toluene, washed successively with 2 N hydrochloric acid, a saturated aqueous solution of sodium bicarbonate and a saturated aqueous solution of sodium chloride, dried over sodium sulphate and evaporated in vacuo. The residue is chromatographed over 30 g of silica gel using 4:1 toluene/ethyl acetate as the running agent and gives diphenylmethyl 3-N,N-diethylcarbamoylmethyl-7$\beta$-[D(—)-($\alpha$-tert.-butoxycarbonylamino-phenylacetylamino]-3-cephem-4-carboxylate, which crystallises from methylene chloride/ethyl acetate/hexane; melting point 204°-205° C.; thin layer chromatogram; Rf value ~0.43 (silica gel; toluene/ethyl acetate, 1:1); UV spectrum (in ethanol): $\lambda_{max}$=258 nm ($\epsilon$=7,500); IR spectrum (Nujol): bands at 2.92, 5.58, 5.79, 5.83, 6.07 and 6.70$\mu$.

(g) 0.66 ml of anisole and 3.80 ml of trifluoroacetic acid are added to a solution of 0.870 g (1.22 mmols) of diphenylmethyl 3-N,N-diethylcarbamoylmethyl-7$\beta$-[D(—)-$\alpha$-tert.-butoxycarbonylamino-phenylacetylamino]-3-cephem-4-carboxylate in 8 ml of methylene chloride, the mixture is stirred for 30 minutes in an ice bath, 100 ml of cold toluene are added and the resulting mixture is evaporated in vacuo. The dry residue is digested with diethyl ether and the precipitate is filtered off and dried in vacuo. The resulting trifluoroacetate of 3-N,N-diethylcarbamoylmethyl-7$\beta$-[D(—)-phenylglycylamino]-3-cephem-4-carboxylic acid is dissolved in a small amount of 1:1 water/methanol and the pH value of the solution is adjusted to 4.6 by adding a 10% strength methanolic solution of triethylamine dropwise. After concentrating the mixture in vacuo, a crystalline product is precipitated by stirring with diethyl ether and, when filtered off and dried under a high vacuum, this product gives the inner salt of 3-N,N-diethylcarbamoylmethyl-7$\beta$-[D(—)-phenylglycylamino]-3-cephem-4-carboxylic acid which has a melting point of 164°-166° C. (decomposition). Thin layer chromatogram: Rf value ~0.32 (silica gel; n-butanol/acetic acid/water, 67:10:23); UV spectrum (in 0.1 N hydrochloric acid) $\lambda_{max}$=256 nm ($\epsilon$=6,200); IR spectrum (in Nujol): bands at 2.88, 3.10, 5.59, 5.87, 5.92, 6.18 and 6.35$\mu$.

EXAMPLE 3

3.82 g (12 mmols) of 1-triphenylphosphoranylidene-2-propanone are added to a solution of 6.15 g (10 mmols) of diphenylmethyl 7$\beta$-[D(—)-$\alpha$-tert.-butoxycarbonylamino-phenylacetylamino]-3-hydroxy-3-cephem-4-carboxylate in 100 ml of toluene and the mixture is warmed to 100° C. for 23 hours. The reaction mixture is evaporated in vacuo and the residue is chromatographed over 300 g of silica gel. Elution with toluene containing 30% of ethyl acetate gives a mixture of isomers consisting of diphenylmethyl 3-acetonyl-7$\beta$-[D(—)-$\alpha$-tert.-butoxycarbonylaminophenylacetylamino]-3-cephem-4-carboxylate and diphenylmethyl 3-acetonylidene-7β-[D(−)-α-tert.-butoxycarbonylamino-phenylacetylamino]-cephem-4-carboxylate; thin layer chromatogram: Rf value ∼0.5 (silica gel; toluene/ethyl acetate, 1:1); IR spectrum (in methylene chloride): bands at 2.95, 5.60, 5.81, 5.89 (shoulder) and 6.67μ.

The resulting mixture of isomers can be further processed as follows:

(a) 805 mg (4.05 mmols) of 85% strength m-chloroperbenzoic acid are added to a solution of 2.4 g (3.68 mmols) of a mixture of isomers consisting of diphenylmethyl 3-acetonyl-7β-[D(−)-α-tert.-butoxycarbonylamino-phenylacetylamino]-3-cephem-4-carboxylate and diphenylmethyl 3-acetonylidene-7β-[D(−)-α-tert.-butoxycarbonylamino-phenylacetylamino]-cepham-4-carboxylate in 45 ml of methylene chloride and the mixture is stirred for 2 hours under nitrogen in an ice bath. The reaction mixture is then washed with water, a saturated aqueous solution of sodium bicarbonate and a saturated aqueous solution of sodium chloride. The organic phase is dried over sodium sulphate and evaporated in vacuo. The residue is recrystallised from ethyl acetate/hexane and gives the 1-oxide of diphenylmethyl 3-acetonyl-7β-[D(−)-α-tert.-butoxycarbonylamino-phenylacetylamino]-3-cephem-4-carboxylate which has a melting point of 206° C.; $[α]_D^{20} = -21 \pm 1°$ (c=0.595; chloroform); UV spectrum (in ethanol): $λ_{max}$=268 nm (ε=5,900); IR spectrum (in Nujol): bands at 2.94, 2.98, 5.57, 5.82 (shoulder), 5.84, 5.95, 6.01, 6.15 and 6.50μ.

(b) 0.35 ml (4 mmols) of phosphorus trichloride is added to a solution of 1.34 g (2.0 mmols) of the 1-oxide of diphenylmethyl 3-acetonyl-7β-[D(−)-α-tert.-butoxycarbonylaminophenylacetylamino]-3-cephem-4-carboxylate in 8 ml of dimethylformamide and the mixture is stirred for 15 minutes at −10° C. The reaction mixture is poured onto ice and extracted with ethyl acetate. The organic phase is washed with a saturated aqueous solution of sodium bicarbonate and a saturated aqueous solution of sodium chloride, dried over sodium sulphate and evaporated in vacuo. The residue is chromatographed over 30 g of silica gel using toluene-ethylacetate mixtures with falling gradients from a 9:1 to a 4:1 relation and gives diphenylmethyl 3-acetonyl-7β-[D(−)-α-tert.-butoxycarbonylamino-phenylacetylamino]-3-cephem-4-carboxylate, which, when recrystallised from acetone/ethyl acetate/hexane, has a melting point of 173°–175°; $[α]_D^{20} = -47° \pm 1°$ (c=0,724; chloroform): UV spectrum (in ethanol): $λ_{max}$=260 nm (ε=7,000); IR spectrum (in Nujol): bands at 2.98, 3.02, 5.62, 5.77, 5.82, 5.93, 5.98 and 6.53μ.

(c) 1.01 ml (9.25 mmols) of anisole and 5.70 ml (80 mmols) of trifluoroacetic acid are added to a solution of 1.21 g (1.85 mmols) of diphenylmethyl 3-acetonyl-7β-[D(−)-α-tert.-butoxycarbonylamino-phenylacetylamino]-3-cephem-4-carboxylate in 12 ml of methylene chloride, the mixture is stirred for 30 minutes in an ice bath, 100 ml of cold toluene are added and the resulting mixture is evaporated in vacuo. The dry residue is digested with diethyl ether and the precipitate is filtered off and dried in vacuo. The resulting trifluoroacetate of 3-acetonyl-7β-[D(−)-phenylglycylamino]-3-cephem-4-carboxylic acid is dissolved in 12 ml of 1:1 water/methanol and the pH value of the solution is adjusted to 4.5 by adding a 10% strength methanolic solution of triethylamine dropwise. The gelatinous mass which has formed is converted, by stirring with diethyl ether, into a microcrystalline product which can be filtered easily and, when filtered off, washed with acetone, methylene chloride and diethyl ether and dried under a high vacuum, this product gives the inner salt of 3-acetonyl-7β-[D(−)-phenylglycylamino]-3-cephem-4-carboxylic acid which has a melting point of ∼195° C. (decomposition). UV spectrum (in 0.1 N hydrochloric acid) $λ_{max}$=260 nm (ε=6,100); IR spectrum (in Nujol): bands at 2.95, 3.12, 5.16, 5.92 and 6.35μ.

EXAMPLE 4

A mixture of 685 mg (1.8 mmols) of diphenylmethyl 7β-amino-3-hydroxy-3-cephem-4-carboxylate and 722 mg (2.7 mmols) of carbomethoxymethylene-triphenylphosphorane in 18 ml of dioxane is warmed to 60° C. for 2 hours under nitrogen. The solvent is evaporated off in vacuo and the residue is purified by preparative silica gel layer chromatography using 95:5 chloroform/methanol as the running agent. Elution of the zone which is visible in UV light with a wavelength of 254 nm and has an Rf value of ∼0.4 gives a mixture consisting of diphenylmethyl 3-carbomethoxymethyl-7β-amino-3-cephem-4-carboxylate and diphenylmethyl 3-carbomethoxymethylene-7β-amino-cepham-4-carboxylate. Thin layer chromatogram: Rf ∼0.4 (silica gel; chloroform/methanol, 95:5); IR spectrum ($CH_2Cl_2$): bands at 2.96, 5.63 and 5.77μ.

EXAMPLE 5

(a) 0.75 ml (5.8 mmols) of isobutyl chloroformate is added to a solution of 2.96 g (4.5 mmols) of diphenylmethyl 3-carboxymethyl-7β-[D(−)-α-tert.-butoxycarbonylamino-phenylacetylamino]-3-cephem-4-carboxylate and 0.51 ml of pyridine in 45 ml of tetrahydrofurane and the mixture is stirred for 30 minutes at −10° C. After adding 0.46 ml of diethylamine, the mixture is stirred for 3 hours at room temperature. The reaction mixture is diluted with ethyl acetate, washed successively with 2 N hydrochloric acid, a saturated aqueous solution of sodium bicarbonate and a saturated aqueous solution of sodium chloride, dried over sodium sulphate and evaporated in vacuo. The residue is chromatographed over 100 g of silica gel using 9:1 toluene/ethyl acetate as the running agent and gives diphenylmethyl 3-carboisobutoxymethyl-7β-[D(−)-α-tert.-butoxycarbonylamino-phenylacetylamino]-3-cephem-4-carboxylate which, when recrystallised from ethyl acetate/hexane, has a melting point of 112°–115° C.; thin layer chromatogram: Rf value ∼0.6 (silica gel; toluene/ethyl acetate, 1:1), UV spectrum (in ethanol): $λ_{max}$=257 nm (ε=7,000); IR spectrum (in $CH_2Cl_2$): bands at 2.94, 5.60, 5.80, 5.89, 6.14 and 6.70μ.

Further elution of the chromatography column with 4:1 toluene/ethyl acetate gives further small amounts of diphenylmethyl 3-N,N-diethylcarbamoylmethyl-7β-[D(−)-α-tert.-butoxycarbonylamino-phenylacetylamino]-3-cephem-4-carboxylate (see Example 2f).

(b) 0.27 ml (2.5 mmols) of anisole and 1.53 ml (2.0 mmols) of trifluoroacetic acid are added to a solution of 0.357 g (0.5 mmol) of diphenylmethyl 3-carboisobutoxymethyl-7β-[D(−)-α-tert.-butoxycarbonylamino-phenylacetylamino]-3-cephem-4-carboxylate in 3 ml of methylene chloride, the mixture is stirred for 30 minutes in an ice bath, 100 ml of cold toluene are added and the resulting mixture is evaporated in vacuo. The residue, which has been dried under a high vacuum, is digested with diethyl ether and the precipitate is filtered off and dried in vacuo. The resulting trifluoroacetate of 3-carboisobutoxymethyl-7β-[D(—)-phenylglycylamino]-3-cephem-4-carboxylic acid is dissolved in 5 ml of 1:1 water/methanol and the pH value of the solution is adjusted to 4.6 by adding 1 N sodium hydroxide dropwise. After concentrating the mixture in vacuo, a beige amorphous powder is precipitated by stirring with diethyl ether and, when it is filtered off and dried under a high vacuum, this powder gives the inner salt of 3-carboisobutoxymethyl-7β-[D(—)-phenylglycylamino]-3-cephem-4-carboxylic acid. Thin layer chromatogram: Rf value ~0.40 (silica gel; n-butanol/acetic acid/water, 67:10:23); UV spectrum (in 0.1 N hydrochloric acid) $\lambda_{max}=258$ nm ($\epsilon=6,000$); IR spectrum (in Nujol): bands at 2.93, 3.10, 5.65, 5.73, 5.87, 6.15, 6.31 and 6.65μ.

EXAMPLE 6

The compounds which follow can be obtained in the manner described above, starting from correspondingly substituted compounds of the formulae II and III and, where appropriate, after carrying out corresponding subsequent operations: 3-carboxymethyl-7β-[D(—)-α-(1,4-cyclohexadienyl)-glycylamino]-3-cephem-4-carboxylic acid, 3-N,N-diethylcarbamoylmethyl-7β-[D(—)-α-(1,4-cyclohexadienyl)glycylamino]-3-cephem-4-carboxylic acid, 3-acetonyl-7β-[D(—)-α-(1,4-cyclohexadienyl)-glycylamino]-3-cephem-4-carboxylic acid, 3-carboisobutoxymethyl-7β-[D(—)-(1,4-cyclohexadienyl)glycylamino]-3-cephem-4-carboxylic acid, 3-carbamoylmethyl-7β-[D(—)-α-(1,4-cyclohexadienyl)-glycylamino]-3-cephem-4-carboxylic acid, 3-N,N-dimethylcarbamoylmethyl-7β-[D(—)-α-phenyl-glycylamino]-3-cephem-4-carboxylic acid, 3-N,N-dimethylcarbamoylmethyl-7β-[D(—)-α-(1,4-cyclohexadienyl)glycylamino]-3-cephem-4-carboxylic acid, 3-hydrazinocarbonylmethyl-7β-[D(—)-α-phenyl-glycylamino]-3-cephem-4-carboxylic acid, 3-hydrazinocarbonylmethyl-7β-[D(—)-α-(1,4-cyclohexadienyl)-glycylamino]-3-cephem-4-carboxylic acid, 3-N-(4-methylpiperazin-1-yl)-carbamoylmethyl-7β-[D(—)-α-phenylglycylamino]-3-cephem-4-carboxylic acid and 3-N-(4-methylpiperazin-1-yl)-carbamoylmethyl-7β-[D(—)-α-(1,4-cyclohexadienyl)-glycylamino]-3-cephem-4-carboxylic acid as well as salts thereof.

EXAMPLE 7

1.80 g (2.74 mmols) of diphenylmethyl 3-carbamoylmethyl-7β-[D(—)-α-(tert.-butoxycarbonylamino)-phenylacetylamino]-3-cephem-4-carboxylate in 20 ml of methylene chloride are stirred with 1.48 ml of anisole and 8.5 ml of trifluoroacetic acid for 30 minutes in an ice bath, 100 ml of cold toluene are added and the mixture is evaporated. The residue is ground with ether to give a pulverulent precipitate, which is filtered off and dried. The resulting trifluoroacetate of 3-carbamoylmethyl-7β-[D(—)-α-phenylglycylamino]-3-cephem-4-carboxylic acid is suspended in 10 ml of water and the pH is adjusted to 4.6 by adding a 10 percent strength methanolic solution of triethylamine, the mixture is stirred for a further 3 hours in an ice bath and the precipitate is filtered off, washed thoroughly several times with ethyl acetate containing 10% of acetone and 10% of ether and dried under a high vacuum, whereupon 3-carbamoylmethyl-7β-[D(—)-α-phenylglycylamino]-3-cephem-4-carboxylic acid is obtained as a pale beige powder which has a melting point of ~150° (with decomposition); Rf 0.35 (on silica gel; using n-butanol:pyridine:acetic acid:water=40:24:6:30; developing with iodine vapour); UV spectrum (in 0.1 N hydrochloric acid): $\lambda_{max}=255$ nm; IR spectrum (in Nujol): bands at, inter alia, 2.93, 3.12, 5.62, 5.90 (shoulder), 5.98, 6.17 (shoulder) and 6.34μ.

The starting material can be obtained as follows: 0.987 g (1.5 mmols) of diphenylmethyl 3-carboxymethyl-7β-[D(—)-α-(tert.-butoxycarbonylamino)-phenylacetylamino]-3-cephem-4-carboxylate in 3 ml of tetrahydrofurane is reacted with 0.309 g (1.5 mmols) of dicyclohexylcarbodiimide for 15 minutes at 0°, 8 ml of a 0.2 N solution of NH₃ in benzene are then added dropwise in the course of 30 minutes and the mixture is allowed to react further for 30 minutes in an ice bath and for 1.5 hours at room temperature. The precipitate which has separated out is filtered off, the filtrate is concentrated and the evaporation residue is worked up by treatment with ethyl acetate, water, sodium bicarbonate and sodium chloride solution. Preparative thin layer chromatography of the crude product on silica gel plates (using 9:1 chloroform/methanol) gives 0.65 g of diphenylmethyl 3-carbamoylmethyl-7β-[D(—)-α-(tert.-butoxycarbonylamino)-phenylacetylamino]-3-cephem-4-carboxylate which, when crystallised from methylene chloride/ethyl acetate/hexane, has a melting point of 128°–130°; Rf ~0.60 (on silica gel; using chloroform/methanol, 9:1); UV spectrum (ethanol): $\lambda_{max}=264$ nm; IR spectrum (methylene chloride): bands at, inter alia, 2.91, 5.60, 5.82, 5.90 (shoulder), 5.94, 6.27 and 6.68μ.

EXAMPLE 8

0.50 g of diphenylmethyl 3-methoxycarbonylmethyl-7β-[D(-)-α-1,4-cyclohexadienyl-α-(tert.-butoxycarbonylamino)-acetamido]-3-cephem-4-carboxylate in 2.5 ml of methylene chloride is stirred with 0.43 ml of anisole and 2.5 ml of trifluoroacetic acid for 30 minutes in an ice bath, under nitrogen, 50 ml of cold toluene are added, the mixture is concentrated in a rotary evaporator, the residue is ground with ether and the trifluoroacetate is filtered off and dried. The latter is suspended in 5 ml of water and extracted with 5 ml of ethyl acetate and, after the organic phase has been separated off, the pH of the aqueous phase is adjusted to about 5 with a 10% strength methanolic solution of triethylamine. After adding 10 ml of acetone, the mixture is left to stand overnight at 0°, the precipitation is brought to completion by adding ether and the precipitate is filtered off, rinsed with acetone/ether (1:1) and dried under a high vacuum, 3-methoxycarbonylmwethyl-7β-[D(-)-α-1,4-cyclohexadienyl-α-amino-acetamido]-3-cephem-4-carboxylic acid being obtained as a pale beige amorphous powder; Rf ~0.39 (on silica gel; using n-butanol/pyridine/glacial acetic acid/water, 40:24:6:30); UV spectrum (in 0.1 N HCl): $\lambda_{max}=258$ nm; IR spectrum (in Nujol): 2.94, 3.14, 5.63, 5.72, 5.85, 6.17, 6.41 and 6.60μ.

The starting material is obtained as follows: 278 mg (1.10 mmols) of tert.-butoxycarbonyl-3,6-dihydrophenylglycine in 2.8 ml of tetrahydrofurane are stirred with 0.12 ml of N-methylmorpholine and 0.15 ml of isobutyl chloroformate for 1 hour at about —10°, a solution, which has been cooled to —10°, of 438.5 mg (1.0 mmol) of diphenylmethyl 3-carbomethoxymethyl-7β-amino-3-cephem-4-carboxylate in 4.3 ml of tetrahydrofurane is then added to the mixed anhydride, the reaction mixture is stirred for 1 hour at about —10° and for 1 hour at room temperature and poured into ice water and the product is taken up in ethyl acetate and extracted by shaking successively with a saturated solution of sodium bicarbonate and a saturated solution of sodium chloride. The resulting crude product is purified by preparative layer chromatography (on silica gel, using toluene/ethyl acetate, 1:1). Diphenylmethyl 3-methoxycarbonylmethyl-7β-[D(-)-α-1,4-cyclohexadienyl-α-(tert.-butoxycarbonylamino)-acetamido]-3-cephem-4-carboxylate, which according to thin layer chromatography is a single compound, is obtained as an amorphous foam; Rf~0.52 (on silica gel using toluene-/ethyl acetate; 1:1); UV spectrum (in ethanol): $\lambda_{max}=261$ nm; IR spectrum (in methylene chloride): 2.98, 5.62, 5.73, 5.84, 5.92, 6.03 and 6.60μ.

EXAMPLE 9

A solution of 0.54 g of the amorphous crude 3-methoxycarbonylmethyl-7β-[D(-)-α-(3-methylsulphonylaminophenyl)-α-(tert.-butoxycarbonylamino)-acetamido]-3-cephem-4-carboxylic acid in 5.4 ml of formic acid is left to stand at room temperature for 1.5 hours and then evaporated in vacuo and the oily residue is digested successively with 5 ml of ether, 5 ml of acetonitrile and 5 ml of acetonitrile/water (95:5). 3β-[D(-)-α-(3-Mesylamnophenyl)-glycylamido]-3-carbomethoxymethyl-3-cephem-4-carboxylic acid is obtained as a pale beige powder; Rf value~0.35 (on silica gel, using n-butanol/pyridine/glacial acetic acid/water, 40:24:6:30); UV spectrum (in 0.1 N HCl): $\lambda_{max}=261$ nm; IR spectrum (in Nujol): 1.9, 2.94, 3.12, 5.62, 5.71, 5.86, 6.17 and 6.60μ.

The starting material can be obtained as follows: 300 mg of diphenylmethyl 3-methoxycarbonylmethyl-7β-amino-3-cephem-4-carboxylate, which can be obtained according to Example 15, in 3 ml of formic acid are stirred at room temperature for 1.5 hours, the mixture is then evaporated in vacuo and the oily residue is digested with 5 ml of ether, 5 ml of acetonitrile and 5 ml of acetonitrile/water. 3-Methoxycarbonylmethyl-7β-amino-3-cephem-4-carboxylic acid is obtained as a pale beige powder; Rf value~0.21 (on silica gel; using n-butanol/pyridine/glacial acetic acid/water, 40:24:6:30); UV spectrum (in 0.1 N HCl): $\lambda_{max}=258$ nm.

A suspension of 0.27 g (1.0 mmol) of 3-methoxycarbonylmethyl-7β-amino-3-cephem-4-carboxylic acid in 5 ml of absolute tetrahydrofurane is stirred with 0.36 ml of aqueous bis-(trimethylsilyl)-acetamide for 1 hour at room temperature, the mixture is cooled to −10° and the mixed anhydride prepared from 379 mg (1.1 mmols) of D(-)-α-(tert.-butoxycarbonylamino)-α-(3-mesylaminophenyl)-acetic acid, 0.15 ml of isobutyl chloroformate and 0.12 ml of N-methylmorpholine in 5 ml of tetrahydrofurane at −15° (1 hour) is added. The mixture is allowed to react for 30 minutes at about −10° and for 1 hour at 0° and is stirred thoroughly with 30 ml of a 1/3 M phosphate buffer which has a pH of 7, the organic solvent is removed by concentrating in vacuo, the aqueous phase is extracted with ethyl acetate, the pH of this phase is then adjusted to 2 with 85% strength $H_3PO_4$ and the mixture is extracted twice with ethyl acetate and the ethyl acetate extracts are extracted by shaking with a saturated solution of sodium chloride, dried over sodium sulphate and evaporated and this gives an amorphous residue of crude 3-methoxycarbonylmethyl-7β-[D(-)-α-(3-methylsulphonylaminophenyl)-α-(tert.-butoxycarbonylamino)-acetamido]-3-cephem-4-carboxylic acid; Rf value~0.64; on silica gel; using n-butanol/pyridine/acetic acid/water, 40:24:6:30).

This acid is processed without further purification.

EXAMPLE 10

2.50 g (3.42 mmols) of diphenylmethyl 3-(N-phenylcarbamoylmethyl)-7β-[D(-)-α-(tert.-butoxycarbonylamino)-phenylacetylamino]-3-cephem-4-carboxylate in 25 ml of methylene chloride are stirred with 1.84 ml of anisole and 10.5 ml (40 equivalents) of trifluoroacetic acid for 30 minutes at 0°, 100 ml of cold toluene are added and the mixture is evaporated in a rotary evaporator. The trifluoroacetate of 3-(N-phenylcarbamoylmethyl)-7β-[D(-)-α-phenylglycylamino]-3-cephem-4-carboxylic acid is obtained when the residue is digested with ether and the precipitate is filtered off. This trifluoroacetate is suspended in 100 ml of water and the pH of the suspension is adjusted to 4.7 by adding a 10 percent strength methanolic solution of triethylamine. The mixture is left to stand at 0° for 5 hours and the fine precipitate is filtered off, rinsed again with acetone and ether and dried under a high vacuum. The resulting 3-(N-phenylcarbamoylmethyl)-7β-[D(-)-α-phenylglycylamino]-3-cephem-4-carboxylic acid melts at 179°–181° (with decomposition); Rf 0.50 (on silica gel; using n-butanol:pyridine:acetic acid:water, 40:24:6:30); UV spectrum (in 0.1 N HCl): $\lambda_{max}=245$ nm; IR spectrum (in Nujol): bands at, inter alia, 2.88, 3.06, 5.66, 5.93, 6.25 and 6.45μ.

The starting material can be obtained as follows: 3.29 g (5 mmols) of diphenylmethyl 3-carboxymethyl-7β-[D(-)-α-(tert.-butoxycarbonylamino)-phenylacetylamino]-3-cephem-4-carboxylate in 25 ml of tetrahydrofurane are stirred with 1.03 g of dicyclohexylcarbodiimide for 30 minutes at 0°, a solution of 0.46 ml (~5 mmols) of aniline in 5 ml of tetrahydrofurane is added and the mixture is stirred for a further 1.5 hours at 0° and for 1 hour at room temperature, the precipitate which has separated out is filtered off, the filtrate is evaporated and the residue is worked up with ethyl acetate, water, a saturated solution of sodium bicarbonate and a saturated solution of sodium chloride. The crude product is recrystallized from methylene chloride/ethyl acetate/hexane and diphenylmethyl 3-(N-phenylcarbamoylmethyl)-7β-[D(-)-α-(tert.-butoxycarbonylamino)-phenylacetylamino]-3-cephem-4-carboxylate, which has a melting point of 134°–136°, is obtained; Rf 0.55 (on silica gel; using toluene/ethyl acetate, 1:1); UV spectrum (in $C_2H_5OH$): $\lambda_{max}=242$ nm; IR spectrum (in methylene chloride): bands at 2.93, 5.58, 5.85 (shoulder), 5.90, 6.24 and 6.68μ.

EXAMPLE 11

2.30 g (3.05 mmols) of diphenylmethyl 3-[N-(2-methyl-1,3,4-thiadiazolyl-5)-carbamoylmethyl]-7β-[D(-)-α-(tert.-butoxycarbonylamino)-phenylacetylamino]-3-cephem-4-carboxylate in 21.5 ml of methylene chloride are stirred with 1.65 ml of anisole and 9.45 ml of trifluoroacetic acid for 30 minutes at 0°, cold toluene (100 ml) is added, the mixture is evaporated, the evaporation residue is ground with ether to give a powder and the latter is filtered off and dried, whereupon the trifluoroacetate of 3-[N-(2-methyl-1,3,4-thiadiazolyl-5)-carbamoylmethyl]-7β-(D(-)-α-phenylglycylamino)-3-cephem-4-carboxylic acid is obtained; the latter is suspended in 10 ml of water and the pH of the suspension is adjusted to 4.6 by adding a 10% strength solution of triethylamine in methanol. After adding ether and stirring the mixture for 2 hours in an ice bath, the precipitate which has separated out is filtered off and washed several times with ethyl acetate/acetone (2:1) and ether and dried, whereupon 3-[N-(2-methyl-1,3,4-thiadiazolyl-5)-carbamoylmethyl]-7β-(D(-)-α-phenylglycylamino)-3-cephem-4-carboxylic acid is obtained as a pale yellowish powder which has a melting point of 185°–190° (with decomposition); Rf 0.32 (on silica gel; using n-butanol:actic acid:water, 67:10:23); UV spectrum (in 0.1 N HCl): $\lambda_{max}$=257 nm; IR spectrum (in Nujol): bands at 3.10, 5.63, 5.90, 6.23 and 6.44μ.

The starting material can be obtained as follows: 3.29 g (5 mmols) of diphenylmethyl 3-carboxymethyl-7β-[D(-)-α-tert.-butoxycarbonylamino)-phenylacetylamino]-3-cephem-4-carboxylate in 40 ml of tetrahydrofurane are stirred with 1.03 g of dicyclohexylcarbodiimide for 30 minutes at −5°, a suspension of 600 mg of 2-amino-5-methyl-1,3,4-thiadiazole in 20 ml of tetrahydrofurane is then added and the mixture is stirred for a further 1 hour at 0° and for a further 2 hours at room temperature. The urea which has precipitated is filtered off, the filtrate is concentrated in a rotary evaporator and the residue is worked up with ethyl acetate, water, sodium bicarbonate solution (saturated) and sodium chloride solution (saturated). Chromatography of the crude product over 120 g of silica gel and elution with toluene/ethyl acetate (1:1) gives diphenylmethyl 3-[N-(2-methyl-1,3,4-thiadiazolyl-5)-carbamoylmethyl]-7β-[D(-)-α-(tert.-butoxycarbonylamino)-phenylacetylamino]-3-cephem-4-carboxylate, which is crystallized from ethyl acetate/ether/hexane; melting point 157°–160°; Rf 0.35 (on silica gel; using chloroform/methanol, 95:5); UV spectrum (in ethanol): $\lambda_{max}$=258 nm; IR spectrum (in Nujol): bands at 3.04, 5.59, 5.78, 5.89, 6.00, 6.40 (shoulder) and 6.54μ.

EXAMPLE 12

1.72 g (3 mmols) of diphenylmethyl 3-(methoxycarbonylmethyl)-7β-phenoxyacetylamino-3-cephem-4-carboxylate in 21 ml of methylene chloride are stirred with 1.62 ml (5 equivalents) of anisole and 9.3 ml (40 equivalents) of trifluoroacetic acid for 30 minutes in an ice bath, 100 ml of cold toluene are added and the mixture is evaporated in a rotary evaporator. The residue is digested with ether and the precipitate which has formed is filtered off, washed with ether and dried. A crude product is obtained and is chromatographed on 10 g of silica gel, which had been deactivated by the addition of 5% of water. Elution with methylene chloride and 20–30% of ethyl acetate gives amorphous 3-(methoxycarbonylmethyl-7β-phenoxyacetylamino-3-cephem-4-carboxylic acid, which according to thin layer chromatography is a single compound; Rf 0.38 (on silica gel; using n-butanol:acetic acid:water, 67:10:23); UV spectrum (in ethanol): $\lambda_{max}$=262, 267 and 274; IR spectrum (in methylene chloride): bands at 2.94, 5.58,5.74, 5.88, 6.11, 6.24, 6.59 and 6.69μ.

The starting material is obtained by the following route:

15.5 g (30 mmols) of diphenylmethyl 3-hydroxy-7β-phenoxyacetylamino-3-cephem-4-carboxylate in 300 ml of toluene are stirred with 12.0 g (1.2 equivalents) of carbomethoxymethylene-triphenylphosphorane for 16 hours at 50°. After evaporating the solvent in a rotary evaporator, the oily residue is chromatographed over 600 g of silica gel and, using toluene and increasing proportions of ethyl acetate (20–30%), diphenylmethyl 3-methoxycarbonylmethyl-7β-phenoxyacetylamino-3-cephem-4-carboxylate, mixed with the isomeric 3-methoxycarbonylmethylene compound, is obtained; Rf 0.5 (on silica gel; using toluene/ethyl acetate, 1:1); IR spectrum (in methylene chloride): bands at 2.94, 6.62, 5.75, 5.83, 6.24 and 6.60μ.

15.5 g (26.2 mmols) of the above mixture are stirred in 325 ml of methylene chloride with 5.85 g (1.1 equivalents) of 85% strength n-chloroperbenzoic acid for 1 hour in an ice bath, the reaction mixture is then diluted with 200 ml of methylene chloride and extracted by shaking successively with water, a saturated solution of sodium bicarbonate and a saturated solution of sodium chloride and the organic phase is dried over sodium sulphate and evaporated. The residual crude product is recrystallised from methylene chloride/ethyl acetate and gives the 1-oxide of diphenyl-methyl 3-methoxycarbonylmethyl-7β-phenoxyacetylamino-3-cephem-4-carboxylate which has a melting point of 195°–197° (with decomposition). A second amount of the crystalline product is obtained from the mother liquor; Rf∼0.15 (on silica gel; using toluene/ethyl acetate, 1:1); UV spectrum (in ethanol): $\lambda_{max}$=268 nm; IR spectrum (in methylene chloride): bands at, inter alia, 2.96, 5.54, 5.75, 5.89, 6.10, 6.24, 6.58 and 6.68μ.

15.1 g (25.7 mmols) of the above sulphoxide in 105 ml of dimethylformamide are stirred with 4.6 ml (51.4 mmols) of phosphorus trichloride for 15 minutes at about −15° and the reaction mixture is poured onto ice and worked up with ethyl acetate, water, a saturated solution of sodium bicarbonate and a saturated solution of sodium chloride. A crude product which, when it is chromatographed over 500 g of silica gel and eluted with toluene and 15–20% of ethyl acetate, gives diphenylmethyl 3-methoxycarbonylmethyl-7β-phenoxyacetylamino-3-cephem-4-carboxylate, which according to thin layer chromatography is a single compound, as a pale yellow foam is obtained; Rf 0.55 (on silica gel, using toluene/ethyl acetate, 1:1); UV spectrum (in ethanol): $\lambda_{max}$=263, 269 and 275 (shoulder); IR spectrum (in methylene chloride): bands at, inter alia, 2.91, 5.57, 5.73, 5.86, 6.10, 6.22, 6.57 and 6.66μ.

EXAMPLE 13

2.70 g (3.90 mmols) of diphenylmethyl 3-methoxycarbonylmethyl-7β-[α-(5-tert.-butoxycarbonylaminomethyl-2-thienyl)-acetylamino]-3-cephem-4-carboxylate in 27 ml of methylene chloride are stirred with 2.5 ml of anisole and 12.1 ml of trifluoroacetic acid for 30 minutes in an ice bath, 100 ml of cold toluene are added, the mixture is evaporated, the residue is digested with ether and the resulting precipitate of the trifluoroacetate of 3-methoxycarbonylmethyl-7β-(5-aminomethyl-2-thienyl)-acetylamino]-3-cephem-4-carboxylic acid is filtered off. When this trifluoroacetate is taken up in 10 ml of water, the mixture is filtered to give a clear solution, the pH of the filtrate is adjusted to 4.6 by adding a 10% strength solution of triethylamine in methanol, the resulting mixture is left to stand for 1 hour in an ice bath and the substance which has precipitated out is filtered off, rinsed with acetone and ether and dried under a high vacuum, this gives 3-methoxycarbonylmethyl-7β-[α-(5-aminomethyl-2-thienyl-acetylamino]-3-cephem-4-carboxylic acid as a micro-crystalline powder which is in the form of the zwitterion and has a melting point of 190°–192° (with decomposition). Rf: 0.12 (on silica gel; using n-butanol:acetic acid:water, 67:10:23); UV spectrum (in 0.1 N HCl): $\lambda_{max}$=243 (14,600) and 270 (shoulder) (5,700); IR spectrum (in Nujol): bands at 2.85, 3.04, 5.68, 5.76 (shoulder), 6.00, 6.15 and 6.50μ.

The starting material is obtained as follows:

438 mg (1 mmol) of diphenylmethyl 3-methoxycarbonylmethyl-7β-amino-3-cephem-4-carboxylate in 10 ml of methylene chloride are stirred with 271 mg of 5-(N-tert.-butoxycarbonylaminomethyl)-2-thienylacetic acid and 206 mg of dicyclohexylcarbodiimide for 5½ hours at room temperature, the precipitate which has separated out is filtered off, the filtrate is evaporated and the residue is purified by preparative thin layer chromatography on silica gel using toluene/ethyl acetate (1:1). Diphenylmethyl 3-methoxycarbonylmethyl-7β-[α-(5-tert.-butoxycarbonylaminomethyl-2-thienyl-acetylamino]-3-cephem-4-carboxylate is obtained and is recrystallised from ethyl acetate/ether/hexane. Melting point: 128°–129°; Rf: 0.46 (on silica gel, using toluene-/ethyl acetate, 1:1); UV spectrum (in ethanol): shoulder at 270 nm, $\lambda_{max}$ 242 nm; IR spectrum (in methylene chloride): bands at 2.92, 5.58, 5.75 (shoulder), 5.83, 5.90 (shoulder) and 6.65μ.

EXAMPLE 14

1.65 g (2.88 mmols) of diphenylmethyl 3-methoxycarbonylmethyl-7β-[D(−)-α-hydroxy-α-phenylacetylamino]-3-cephem-4-carboxylate in 20 ml of methylene chloride are stirred with 0.77 ml (3 equivalents) of anisole and 4.4 ml (20 equivalents) of trifluoroacetic acid for 30 minutes in an ice bath, 100 ml of cold toluene are added, the mixture is evaporated in a rotary evaporator and the residue is digested with ether and this gives a brownish powder which contains the crude product, which is reprecipitated from acetone/ether/hexane for purification. 3-Methoxycarbonylmethyl-7β-[D(−)-α-hydroxy-α-phenylacetylamino]-3-cephem-4-carboxylic acid, which according to thin layer chromatography is a single compound, is obtained as a colourless micro-crystalline powder; Rf 0.31 (on silica gel; using n-butanol:acetic acid:water, 67:10:23); UV spectrum (in ethanol): $\lambda_{max}$ 257 nm; IR spectrum (in Nujol): bands at 2.90, 3.00, 5.62, 5.77, 5.92, 5.95 (shoulder), 6.08 and 6.57μ.

The starting material is obtained as follows:

4.4 ml of pyridine and 44 ml of an 8% strength suspension of phosphorus pentachloride in methylene chloride are added to a solution, which has been cooled to −17°, of 3.10 g (5.42 mmols) of diphenylmethyl 3-methoxycarbonylmethyl-7β-phenoxyacetylamino-3-cephem-4-carboxylate in 110 ml of methylene chloride and the mixture is then stirred for 3 hours in an ice bath. After cooling to −30°, 27 ml of absolute methanol are added and the residue mixture is stirred for 1 hour at −10°, for 1 hour at 0° and for 1 hour at room temperature. The pH is adjusted to 2.5 by adding a 0.5 M solution of potassium dihydrogen phosphate, the mixture is stirred for a further 0.5 hour and, for working up, the organic phase is separated off, the aqueous phase is subsequently extracted with twice 50 ml of methylene chloride and the combined methylene chloride phases are extracted by shaking with a saturated solution of sodium chloride, dried over sodium sulphate and evaporated. Chromatography of the crude product over 100 g of silica gel and elution with toluene and 20–30% of ethyl acetate gives amorphous diphenylmethyl 3-methoxycarbonylmethyl-7β-amino-3-cephem-4-carboxylate, which according to thin layer chromatography is a single compound and which is characterised in the form of the crystalline toluenesulphonate; melting point 157°–158° (decomposition); Rf 0.45 (on silica gel, with ethyl acetate); UV spectrum (in ethanol): $\lambda_{max}$=257 nm; IR spectrum (in Nujol): bands at 2.87, 5.57, 5.72, 5.79 and 6.12μ.

438 mg (1 mmol) of the above product in 10 ml of methylene chloride are allowed to react with 356 mg (∼2 mmols) of D-(−)-mandelic acid O-carboxyanhydride for 1 hour at room temperature and the reaction mixture is evaporated. Preparative thin layer chromatography of the residue (over silica gel; using toluene-/ethyl acetate (1:1); rendered visible with UV light at 254 nm) gives amorphous diphenylmethyl 3-methoxycarbonylmethyl-7β-[D(−)-α-hydroxy-α-phenylacetylamino]-3-cephem-4-carboxylate, which according to thin layer chromatography is a single compound; Rf 0.35 (on silica gel; using toluene/ethyl acetate, 1:1); UV spectrum (in ethanol): $\lambda_{max}$=268 nm; IR spectrum (in methylene chloride): bands at, inter alia, 2.91, 2.94, 5.59, 5.73, 5.85, 6.24 and 6.60μ.

EXAMPLE 15

0.50 ml of anisole and 6.5 ml of trifluoroacetic acid are added to 1.85 g of diphenylmethyl 3-[N-(5-tert.-butoxycarbonylamino-5-tert.-butoxycarbonylpentyl)-carbamoylmethyl]-7β-[D(−)-α-(tert.-butoxycarbonylamino)-α-phenylacetylamino]-3-cephem-4-carboxylate and the mixture is brought into solution by adding about 5 ml of methylene chloride, the solution is stirred for 4.5 hours at room temperature and, after adding 150 ml of toluene, the mixture is evaporated and the residue is ground with ether to give a fine precipitate, which is filtered off and dried. The crude product which is thus obtained is dissolved in a little water and purified by taking up the solution in a column containing 200 ml of a non-ionic absorbent (for example Amberlite ®-XAD-2), separating off water-soluble salts, such as trifluoroacetates, by washing with water and then eluting with water/isopropanol (85:15), and the fractions obtained on thin layer chromatography of the product are combined, concentrated in vacuo and then lyophilised. 3-[N-(5-amino-5-carboxypentyl)-carbamoylmethyl]-7β-[D(−)-α-phenylglycylamino]-3-cephem-4-carboxylic acid is obtained as a colourless lyophilised product which has an Rf of 0.23 (on silica gel; using n-butanol:pyridine:acetic acid:water, 40:24:6:30); UV spectrum (in ethanol): $\lambda_{max}$=266 nm; IR spectrum (in Nujol): bands at, inter alia, 2.95, 3.12, 5.64, 5.88 (shoulder), 6.13 and 6.36μ.

The starting material can be obtained as follows:

A solution of 3.28 g (∼5 mmols) of diphenylmethyl 3-carboxymethyl-7β-[D(−)-α-tert.-butoxycarbonylamino-α-phenylacetylamino]-3-cephem-4-carboxylate in 25 ml of tetrahydrofurane is stirred with 1.03 g of dicyclohexylcarbodiimide for 30 minutes at −5°, a solution of the tert.-butyl ester of $N^\alpha$-(tert.-butoxycarbonyl)-lysine in 10 ml of tetrahydrofurane is added and the mixture is stirred for a further 1.5 hours at about −5° and for 1 hour in an ice bath and for 2 hours at room temperature, the urea which has precipitated out is filtered off, the filtrate is evaporated in a rotary evaporator and the residue is worked up with ethyl acetate, water, sodium bicarbonate solution and sodium chloride solution. chromatography of the crude product over 140 g of silica gel and elution with toluene/ethyl acetate (3:1) gives diphenylmethyl 3-[N-(5-tert.-butoxycarbonylamino-5-tert.-butoxycarbonylpentyl)-carbamoylmethyl]-7β-[D(−)-α-tert.-butoxycarbonylamino-α-phenylacetylamino]-3-cephem-4-carboxylate as an amorphous foam, which is precipitated from ethyl acetate/ether/hexane; Rf 0.40 (on silica gel; using toluene/ethyl acetate, 1:1); UV spectrum (in ethanol): $\lambda_{max}=268$ nm; IR spectrum (in methylene chloride): bands at, inter alia, 2.94, 5.63, 5.74, 5.85, 5.88 (shoulder), 6.24 and 6.65μ.

EXAMPLE 16

Dry ampoules or phials containing 0.5 g of the inner salt of 3-carbomethoxymethyl-7β-[D(—)-α-phenylglycylamino]-3-cephem-4-carboxylic acid are manufactured as follows:

| Composition (for 1 ampoule or phial) | |
|---|---|
| inner salt of 3-carbomethoxymethyl-7β-[D(—)-α-phenylglycylamino]-3-cephem-4-carboxylic acid | 0.5 g |
| mannitol | 0.05 g |

A sterile aqueous solution of the inner salt of 3-carbomethoxymethyl-7β-[D(—)-α-phenylglycylamino]-3-cephem-4-carboxylic acid and of the mannitol is subjected to freeze drying under aseptic conditions in 5 ml ampoules or 5 ml phials and the ampoules or phials are sealed and tested.

EXAMPLE 17

Capsules containing 0.25 g of the inner salt of 3-carbomethoxymethyl-7β-[D(—)-α-phenylglycylamino]-3-cephem-4-carboxylic acid are manufactured as follows:

| Composition (for 1,000 capsules): | |
|---|---|
| inner salt of 3-carbomethoxymethyl-7β-[D(—)-α-phenylglycylamino]-3-cephem-4-carboxylic acid | 250.000 g |
| maize starch | 50.000 g |
| polyvinylpyrrolidone | 15.000 g |
| magnesium stearate | 5.000 g |
| ethanol | q.s. |

The inner salt of 3-carbomethoxymethyl-7β-[D(—)-α-phenylglycylamino]-3-cephem-4-carboxylic acid and the maize starch are mixed and the mixture is moistened with a solution of the polyvinylpyrrolidone in 50 g of ethanol. The moist mass is pressed through a sieve with a mesh width of 3 mm and dried at 45°. The dry granules are forced through a sieve with a mesh width of 1 mm and mixed with 5 g of magnesium stearate. The mixture is filled, in portions of 0.325 g, into push-fit capsules.

What is claimed is:

1. A member selected from the group consisting of 7β-amino-3-cephem-3-carbonylmethyl-4-carboxylic acid compounds of the formula

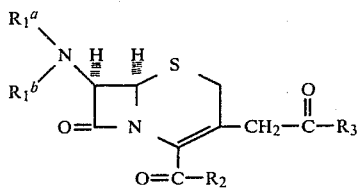

and corresponding 7β-amino-3-carbonylmethylene-cephem-4-carboxylic acid compounds of the formula

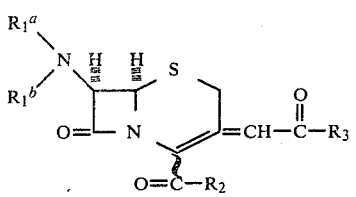

and 1-oxides and pharmacologically acceptable salts of such compounds, in which $R_1{}^a$ represents a member selected from the group consisting of hydrogen and an acyl radical of the formula A

in which $R_a$ represents phenyl, thienyl, furyl, cyclohexadienyl or cyclohexenyl or phenyl, thienyl, furyl, cyclohexadienyl or cyclohexenyl, substituted by aminomethyl, in which the amino group may be free or protected by one of the amino protecting groups triphenylmethyl, tri-lower alkylsilyl or tri-lower alkylstannyl, lower alkoxy carbonyl, which is multiple branched and/or phenyl substituted in the α-position, benzoylmethoxycarbonyl, a lower alkoxycarbonyl substituted in the β-position by halogen atoms, adamamtyloxycarbonyl, lower alkoxy-carbonyl mono- or polysubstituted in the α-position by phenyl or p-nitrophenyl, and furyloxycarbonyl, or phenyl substituted by hydroxyl, or amino lower alkylated or sulphonated, or amino protected by an amino protecting group as defined above, $R_b$ represents hydrogen and $R_c$ represents hydrogen, hydroxyl, or hydroxyl protected by one of the hydroxyl protecting groups, lower-alkoxy-carbonyl which is multiple branched and/or phenyl substituted in the α-position, benzoyl-methoxycarbonyl, a lower alkoxycarbonyl, substituted in the β-position by halogen atoms, adamamtyloxycarbonyl, lower alkoxy-carbonyl mono- or polysubstituted in the α-position by phenyl or p-nitrophenyl, furfuryloxycarbonyl, tri-lower alkylsubstituted silyl or stannyl and benzyl or diphenylmethyl, unsubstituted or substituted by methoxy, halogen, or nitro, an amino group, an amino group protected as mentioned before, and sulpho, or sulpho protected by tri-loweralkyl-silyl- or stannyl, by nitrobenzyl or by diphenylmethyl, or a group (A) in which $R_a$ represents cyano, pyridylthio, tetrazolyl, phenoxy or phenoxy in which phenyl is substituted like a phenyl group $R_a$, and $R_b$ and $R_c$ each represent hydrogen, or a group (A), in which $R_a$ represents phenyl, thienyl, furyl, and $R_b$ and $R_c$ together denote lower alkoxyimino, cycloalkoxyimino and phenyl-lower alkoxyimino in the syn-configuration, $R_1{}^b$ represents hydrogen, $R_2$ represents hydroxyl, α-poly-branched lower alkoxy, 2-iodo-lower alkoxy, phenacyloxy, 1-phenyl-lower alkoxy which has 1-3 phenyl radicals, or 1-3 phenyl radicals which are substituted by lower alkoxy or nitro, lower alkanoyloxymethoxy, α-amino-lower alkanoyloxymethoxy or 2-phthalidyloxy, or tris-lower alkylsilyloxy, and $R_3$ represents hydrogen, lower alkyl, cycloalkyl, phenyl, phenyl substituted by lower alkyl, lower alkoxy or halogen, phenyl-lower alkyl, in which the phenyl nucleus is unsubstituted or substituted by nitro, lower alkyl, lower alkoxy or halogen, hydroxyl, lower alkoxy, amino, lower alkylamino, di-lower alkylamino, lower alkyleneamino, oxa-lower alkylenamino, phenylamino, hydroxylamino, lower alkoxyamino, hydrazino, 2- lower alkylnydrazino, 2-phenylhydrazino, 2-phenylhydrazino, 4-lower alkylpiperazin-1-ylamino, lower alkylamino wherein loweralkyl is substituted by amino and carboxyl, lower alkylamino wherein lower alkyl is substituted by carboxyl, or heterocyclylamino, wherein the heterocycyl radical is selected from the group consisting of pyridyl, pyridyl-1-oxide, pyrazinyl, pyrimidyl, pyridazinyl, thiadiazolyl, 2-methylthiadiazolyl, oxadiazolyl, tetrazolyl or N-methyl tetrazolyl.

2. A compound according to claim 1 and being a member of the group of compounds of the formula IA and of the formula IB and also the 1-oxides thereof or pharmacologically acceptable salts of such compounds in which $R_1$ represents hydrogen or an acyl group of the formula (A), in which $R_a$ denotes phenyl, hydroxyphenyl, 3-lower alkylsulphonylaminophenyl, or aminomethylphenyl, aminomethylphenyl, wherein amino is protected as defined in claim 1, and also denotes thienyl, aminomethylthienyl, furyl, aminomethylfuryl, 1,4-cyclohexadienyl, aminomethyl-1,4-cyclohexadienyl, 1-cyclohexenyl or aminomethyl-1-cyclohexenyl, $R_b$ represents hydrogen and $R_c$ represents hydrogen, amino, protected amino as defined in claim 1, hydroxyl, protected hydroxyl as defined in claim 1, and sulpho, or in which $R_a$ represents cyano, 1-tetrazolyl, phenoxy or 4-pyridylthio and $R_b$ and $R_c$ each represent hydrogen, or in which $R_a$ represent phenyl, 2-thienyl and 2-furyl and $R_b$ and $R_c$ together denote syn-lower alkoximino, $R_{1b}$ denotes hydrogen, $R_2$ represents hydroxyl, α-poly-branched lower alkoxy, 2-halogeno-lower alkoxy, or diphenylmethoxy which is unsubstituted or substituted by lower alkoxy, or p-nitrobenzyloxy, or tri-lower alkylsilyloxy, and $R_3$ denotes hydrogen, lower alkyl with 1 to 4 carbon atoms, phenyl, hydroxyl, lower alkoxy, 2-halogeno-lower alkoxy, diphenylmethoxy, diphenylmethoxy substituted in the phenyl rings by methoxy or nitro, benzyloxy or benzyloxy substituted by methoxy or nitro, amino, lower alkylamino, di-lower alkylamino, lower alkyleneamino, oxa-lower alkyleneamino, phenylamino, hydroxylamino, lower alkoxyamino, hydrazino, 2-lower alkylhydrazino, 2-phenyl-hydrazino, 4-lower alkylpiperazin-1-ylamino, aminocarboxy-lower alkylamino, 1,3,4-thiadiazolylamino, 2-methyl 1,3,4-thiadiazolylamino, 5-tetrazolylamino and 1-methyl-5-tetrazolylamino.

3. An antibiotically effective composition comprising antibiotically effective amount of a compound of formula IA, as claimed in claim 1 or a pharmacologically acceptable salt thereof, together with excipients which can be used pharmaceutically.

4. A method for the treatment of systemic infections by gram-positive and gram-negative bacteria comprising administration of an antibiotically effective amount of a compound of the formula IA as claimed in claim 1.

5. A compound according to claim 1 and being a member of the group 3-Carbomethoxymethyl-7β-[D(—)-α-(3-methylsulphonylaminophenyl)-glycylamino]-3-cephem-4-carboxylic acid and a pharmacologically acceptable salt thereof.

6. A compound according to claim 1 and being a member of the group 3-Carbomethoxymethyl-7β-[D(—)-α-phenylglycylamino]-3-cephem-4-carboxylic acid and a pharmacologically acceptable salt thereof.

7. A compound according to claim 1 and being a member of the group 3-Carbomethoxymethyl-7β-[D(—)-α-(1,4-cyclohexadienylglycylamino)]-3-cephem-4-carboxylic acid and a pharmacologically acceptable salt thereof.

8. A compound according to claim 1 and being a member of the group 3-p-Nitrocarbobenzyloxymethyl-7β-(D(—)-α-phenylglycylamino)-3-cephem-4-carboxylic acid and a pharmacologically acceptable salt thereof.

9. A compound according to claim 1 and being a member of the group comprising Diphenylmethyl 3-carboxymethyl-7β-[D(—)-α-tert.-butoxycarbonylaminophenylacetylamino]-3-cephem-4-carboxylate.

10. A compound according to claim 1 and being a member of the group 3-Carboxymethyl-7β-[D(—)-α-phenylglycylamino]-3-cephem-4-carboxylic acid and a pharmacologically acceptable salt thereof.

11. A compound according to claim 1 and being a member of the group 3-N,N-Diethylcarbamoylmethyl-7β-[D(—)-α-phenylglycylamino]-3-cephem-4-carboxylic acid and a pharmacologically acceptable salt thereof.

12. A compound according to claim 1 and being a member of the group 3-Acetonyl-7β-[D(—)-phenylglycylamino]-3-cephem-4-carboxylic acid and a pharmacologically acceptable salt thereof.

13. A compound according to claim 1 and being a member of the group Diphenylmethyl 3-carbomethoxymethyl-7β-amino-3-cephem-4-carboxylate and a pharmacologically acceptable salt thereof.

14. A compound according to claim 1 and being a member of the group 3-Carboisobutoxymethyl-7β-[D(—)-phenylglycylamino]-3-cephem-4-carboxylic acid and a pharmacologically acceptable salt thereof.

15. A compound according to claim 1 and being a member of the group 3-Carbamoylmethyl-7β-[D(—)-α-phenylglycylamino]-3-cephem-4-carboxylic acid and a pharmacologically acceptable salt thereof.

16. A compound according to claim 1 and being a member of the group 3-Anilinocarbonylmethyl-7β-[D(—)-α-phenylglycylamino]-3-cephem-4-carboxylic acid and a pharmacologically acceptable salt thereof.

17. A compound according to claim 1 and being a member of the group 3-[(2-Methyl-1,3,4-thiadiazolyl-5-amino)-carbonylmethyl]-7β-[D(—)-α-phenylglycylamino]-3-cephem-4-carboxylic acid and a pharmacologically acceptable salt thereof.

18. A compound according to claim 1 and being a member of the group 3-Carbomethoxymethyl-7β-phenoxyacetylamino-3-cephem-4-carboxylic acid and a pharmacologically acceptable salt thereof.

19. A compound according to claim 1 and being a member of the group 3-Carbomethoxymethyl-7β-[α-(5-aminomethyl-2-thienyl)-acetylamino]-3-cephem-4-carboxylic acid and a pharmacologically acceptable salt thereof.

20. A compound according to claim 1 and being a member of the group 3-Carbomethoxymethyl-7β-[D(—)-α-hydroxy-α-phenylacetylamino]-3-cephem-4-carboxylic acid and a pharmacologically acceptable salt thereof.

21. A compound according to claim 1 and being a member of the group 3-(5-Amino-5-carboxypentylaminocarbonylmethyl)-7β-[D(—)-α-phenylglycylamino]-3-cephem-4-carboxylic acid and a pharmacologically acceptable salt thereof.

22. A compound according to claim 1, and being a member selected from the group consisting of compounds of the formula IA and pharmacologically acceptable salts of such compounds, in which $R_1{}^a$ represents hydrogen or an acyl radical of the formula A $$R_a-C(R_b)(R_c)-C(=O)- \qquad (A),$$

in which $R_a$ represents phenyl, thienyl, furyl, cyclohexadienyl, cyclohexenyl, cyclohexenyl substituted by aminomethyl, or phenoxy or pyridylthio, $R_b$ denotes hydrogen and $R_c$ denotes hydrogen, hydroxy or amino, $R_1{}^b$ represents hydrogen, $R_2$ represents hydroxy, α-polybranched-lower alkoxy, 2-halogeno-lower alkoxy, lower alkanoyloxymethoxy, lower alkoxy substituted or unsubstituted in the 1-position by one to three phenyl radicals, which are unsubstituted or substituted by lower alkoxy or nitro, or trislower alkylsilyloxy and $R_3$ represents hydrogen, lower alkyl, cycloalkyl, phenyl unsubstituted or substituted by lower alkyl, lower alkoxy or halogen, phenyl-lower alkyl unsubstituted or substituted by nitro, lower alkoxy or halogen, hydroxy, lower alkoxy, lower alkanoyloxymethoxy, amino, lower alkylamino, dilower alkylamino, piperidino, morpholino, piperazino unsubstituted or substituted by lower alkyl, anilino, hydroxylamino, lower alkoxamino, hydrazino, 2-lower alkylhydrazino, lower alkylamino, unsubstituted or substituted by amino and/or carboxyl, and heterocyclylamino of the group pyridyl, pyridyl-1-oxide, pyrazinyl, pyrimidyl, pyridazinyl, thiadiazolyl, 2-methylthiadiazolyl, oxadiazolyl, tetrazolyl, or N-methyltetrazolyl.

23. A compound according to claim 1 and being a member of the group of 7β-(D-α-amino-α-$R_a$-acetylamino)-3-R-carbonylmethyl-3-cephem-4-cephem-4-carboxylic acids of formula Ia in which $R_a$ represents phenyl, 4-hydroxyphenyl, 3-methylsulphonylaminophenyl, 2-thienyl, 1,4-cyclohexadienyl and 1-cyclohexenyl and $R_3$ represents methyl, methoxy, phenyl, amino, dimethylamino, phenylamino, pyrrolidino, morpholino, hydrazino, 2-phenylhydrazino, 4-methyl-piperazin-1-ylamino, aminocarboxypentylamino and 2-methyl-5-(1,3,4-thiadiazolyl)-amino, and pharmacologically acceptable salts thereof.

* * * * *